(12) United States Patent
Hoang et al.

(10) Patent No.: US 10,888,376 B2
(45) Date of Patent: Jan. 12, 2021

(54) SURGICAL LASER SYSTEM

(71) Applicant: Convergent Laser Technologies, Alameda, CA (US)

(72) Inventors: Anh Ngoc Hoang, San Jose, CA (US); John L. Rink, San Francisco, CA (US)

(73) Assignee: Convergent Laser Technologies, Alameda, CA (US)

( * ) Notice: Subject to any disclaimer, the term of this patent is extended or adjusted under 35 U.S.C. 154(b) by 0 days.

(21) Appl. No.: 15/973,545

(22) Filed: May 8, 2018

(65) Prior Publication Data

US 2019/0343584 A1    Nov. 14, 2019

(51) Int. Cl.
*A61B 18/20* (2006.01)
*A61B 18/22* (2006.01)
*A61B 18/00* (2006.01)
*A61B 34/30* (2016.01)

(52) U.S. Cl.
CPC .............. *A61B 18/22* (2013.01); *A61B 34/30* (2016.02); *A61B 2018/00577* (2013.01); *A61B 2018/00589* (2013.01); *A61B 2018/00601* (2013.01); *A61B 2018/00619* (2013.01); *A61B 2018/00625* (2013.01); *A61B 2018/00791* (2013.01); *A61B 2018/20355* (2017.05); *A61B 2018/20361* (2017.05)

(58) Field of Classification Search
None
See application file for complete search history.

(56) References Cited

U.S. PATENT DOCUMENTS

| | | | | |
|---|---|---|---|---|
| 6,128,524 A * | 10/2000 | Yoneya | .................. | A61B 3/145 514/410 |
| 7,292,759 B2 * | 11/2007 | Boutoussov | ........... | A61B 18/20 385/117 |
| 8,449,587 B2 * | 5/2013 | Cornil | .................. | A61B 18/203 607/89 |
| 9,134,243 B2 * | 9/2015 | Wilson | ................. | A61B 5/0059 |
| 2008/0033300 A1 * | 2/2008 | Hoang | ................... | A61B 18/20 600/474 |
| 2008/0226029 A1 * | 9/2008 | Weir | .................. | A61B 1/00172 378/65 |
| 2008/0312490 A1 * | 12/2008 | Cropper | ............... | A61B 1/0623 600/3 |
| 2009/0062718 A1 * | 3/2009 | Cornil | .................. | A61B 18/203 604/20 |
| 2012/0232534 A1 * | 9/2012 | Rink | ...................... | A61B 18/24 606/3 |
| 2015/0157209 A1 * | 6/2015 | Dantus | ................. | A61B 5/0071 600/317 |

* cited by examiner

*Primary Examiner* — Michael W Kahelin
*Assistant Examiner* — Shirley X Jian
(74) *Attorney, Agent, or Firm* — Patent2ip LLC

(57) ABSTRACT

A surgical laser system can include a fluorescent sensing assembly for detecting fluorescent signal from a tissue under a surgical operation of the surgical laser system. The surgical laser system can include an aiming laser assembly, which can be configured to provide excitation energy for the fluorescent process. The surgical laser system can include an infrared sensing assembly, which can provide temperature related data, for example, to prevent damages to the tissue due to overheating. The surgical laser system can be configured to use the off-time of the surgical laser for tissue sensing. Data from tissue sensing can be further analyzed by an integrated robotic surgical system to provide a highly precise surgical procedure.

17 Claims, 21 Drawing Sheets

Forming a surgical laser system, wherein the surgical laser system comprises a surgical laser, an aiming laser assembly having one or more frequencies, a fluorescent sensor, and a controller coupling an output of the fluorescent sensor to the surgical sensor, wherein the aiming laser assembly is configured to excite tissue to stimulate tissue fluorescence that can be detected by the fluorescent sensor, wherein the controller is configured to use fluorescent data from the fluorescent sensor to determine characteristics of the tissue to control the surgical laser
400

*FIG. 4A*

Forming a surgical laser system having a controller for controlling operating conditions of the surgical laser
420

↓

Coupling a fluorescent sensor to the surgical laser system, wherein the fluorescent sensor is configured to detect auto-fluorescent signal emitted by a tissue excited by an aiming laser of the surgical laser system
430

↓

Configuring the controller for processing an output of the fluorescent sensor to determine characteristics of the tissue, wherein the characteristics of the tissue is configured to assist the controller in determining at least an operating condition of the surgical laser
440

*FIG. 4B*

Using an aiming laser of a surgical laser system to excite tissue that is aimed at by the aiming laser, wherein the excited tissue is configured to undergo fluorescent emission, wherein the fluorescent emission is configured to optimize a surgical laser system for the tissue
500

FIG. 5A

Using detected fluorescent emission from tissue to optimize a surgical laser system for the tissue, wherein the tissue is excited by an aiming laser of the surgical laser system
520

FIG. 5B

Aiming at a tissue using an aiming laser of a surgical laser system, wherein the aiming laser also excites the tissue to stimulate a tissue fluorescent process
540

Detecting fluorescent signal emitted by the tissue
550

Optimizing the surgical laser system for operating on the tissue based on the detected fluorescent signal
560

FIG. 5C

Forming a switching assembly for switching between different color aiming lasers of a surgical laser system having fluorescent characterization of tissue, wherein the switching assembly comprises a rotation assembly
800

*FIG. 8A*

Forming a mixing assembly for mixing different color aiming lasers of a surgical laser system having fluorescent characterization of tissue
820

*FIG. 8B*

Forming a spectral fluorescent sensing assembly for assessing fluorescent signal from a surgical laser system having multiple frequency aiming laser assembly
840

*FIG. 8C*

Integrating a surgical laser system having multiple frequency aiming laser assembly to a surgical robotic system
860

*FIG. 8D*

```
┌─────────────────────────────────────────────┐
│ Setting an operating condition of a surgical │
│ laser system based on a tissue temperature  │
│ or a rate in the tissue temperature         │
│ 1200                                        │
└─────────────────────────────────────────────┘
```

FIG. 12A

```
┌─────────────────────────────────────────────┐
│ Obtaining a tissue temperature or a rate of │
│ change of the tissue temperature under an   │
│ operation of a surgical laser system        │
│ 1220                                        │
└─────────────────────────────────────────────┘
                      │
                      ▼
┌─────────────────────────────────────────────┐
│ Changing an operating condition of the      │
│ surgical laser system to obtain a steady    │
│ tissue temperature during the operation     │
│ 1230                                        │
└─────────────────────────────────────────────┘
```

FIG. 12B

```
┌─────────────────────────────────────────────┐
│ Obtaining a tissue temperature or a rate of │
│ change of the tissue temperature under an   │
│ operation of a surgical laser system        │
│ 1250                                        │
└─────────────────────────────────────────────┘
                      │
                      ▼
┌─────────────────────────────────────────────┐
│ Changing an operating condition of the      │
│ surgical laser system to prevent            │
│ irreversible tissue damage caused by the    │
│ operation                                   │
│ 1260                                        │
└─────────────────────────────────────────────┘
```

FIG. 12C

SURGICAL LASER SYSTEM

BACKGROUND

Laser systems can be used to perform various surgical operations in humans and animals. Recent developments of laser surgical systems and methods have demonstrated that laser surgery can offer precision and speed which cannot be achieved by manual and mechanical surgical methods. In laser surgery, laser pulses interact with a target tissue to selectively remove or disrupt the tissue undergoing the surgical procedures, using short duration laser pulses with selective frequencies and energy per pulse. The short pulse laser systems shall require precise control of pulse width, energy per pulse, and aiming beam pulses.

FIGS. 1A-1B illustrate prior art surgical laser systems according to some embodiments. FIG. 1A shows a basic laser design layout for fiber delivery system. The surgical laser system 100 can include a surgical laser 110 together with an optical assembly to bring the output of the surgical laser 110 to an optical fiber 108, the distal end of which can be inserted inside a patient for surgical operations. The optical assembly can include a mirror 101 and a beam splitter 102, which can split the output of the surgical laser to the optical fiber 108 and also to an internal energy sensor 115 for measuring the output power of the surgical laser. The optical assembly can include an output lens 107 for focusing the laser beam emitted from the surgical laser. The optical assembly can also include other components, such as a laser beam guiding assembly for guiding the laser beam. The surgical laser system can include an aiming laser assembly, which can include a blue laser aiming beam 120 and a green aiming laser 121, which can reach optical elements, such as mirrors and/or beam splitters 103 and 104 to combine with the surgical laser beam (treatment beam). The laser system can activate one color aiming laser at a time, such as turning on the blue laser while turning off the green laser. The aiming beam can be a diode laser or high power focused LED.

FIG. 1B shows another laser system arrangement 105. The surgical laser 110 can be mounted to provide a laser beam directly to the beam splitter 102, instead of reflecting from the mirror 101.

SUMMARY OF THE EMBODIMENTS

In some embodiments, the present invention discloses a surgical laser system to perform surgical operations for patients. The surgical laser system can include a surgical laser assembly having a surgical laser, e.g., a laser configured to perform the surgery, such as operating on the patient tissues.

The surgical laser system can include an optical assembly, which can be configured to deliver an output of the surgical laser to the tissue.

The surgical laser system can include a surgical laser controller, which can be configured to control the surgical laser assembly, such as to control the power, pulse rates and pulse widths of the surgical laser.

The surgical laser system can include an aiming laser assembly, which can include one or more aiming lasers, e.g., lasers configured to aim and mark the tissue under the surgical operation. The aiming laser assembly can include multiple lasers having different colors, such as red, blue and green. The aiming laser assembly can include an aiming laser controller, which can be configured to control a selection of the lasers, such as for selectively delivering one laser (e.g., output of one laser) or a combination of lasers (e.g., a combination of the outputs of two or more lasers). The aiming laser controller can be configured for controlling the power, the pulse rates, and the pulse widths of the lasers. The aiming laser controller can be configured for communicating with the surgical laser controller, e.g., the surgical laser controller can determine the selection of aiming lasers, the power, pulse rates, and pulse widths of the aiming lasers through the communication.

The surgical laser system can include a fluorescent sensing assembly, which can be configured to detect a fluorescent signal emitted from the tissue, such as the tissue aiming at by the aiming laser and to undergo a surgical operation by the surgical laser. The excitation energy can be provided by the aiming laser assembly. For example, in an auto-fluorescent process, the tissue is excited by the aiming laser, so that when the tissue molecules decay, fluorescent signals can be emitted. Fluorescent dies can be provided to the tissue, so that the dies can be excited for emitting the fluorescent signal. The output of the fluorescent sensing assembly can be provided to the surgical laser controller and an attached robotic system, for example, to assist in the minimally invasive surgical process. The fluorescent sensing assembly can include a hyperspectral or multispectral fluorescent sensor, for obtaining fluorescent signals at different excitation energies.

The fluorescent sensing assembly can communicate with the aiming laser controller, for example, to provide appropriate excitation energies to generate the fluorescent signal. Alternatively, the surgical laser controller can communicate with the aiming laser controller. Thus the fluorescent sensing assembly can provide data to the surgical laser controller and the external robotic system.

The surgical laser controller can be configured to process the fluorescent signal for assistance in controlling the laser energy output to the target tissue. For example, the surgical laser controller can be configured to provide processed information from the fluorescent signal to a display, or to control at least one of a power, a pulse rate, and a pulse width of the surgical laser output.

The surgical laser system can further include at least one of a near infrared imaging assembly and a Raman spectrometer for characterizing the tissue such as tumors or cancerous tissues.

The surgical laser system can also include an infrared sensing assembly, which can be configured to measure a temperature or a rate of temperature of the target tissue. The output of the infrared sensing assembly can be provided to the surgical laser controller, to assist in the surgical operation. For example, the surgical laser controller can be configured to control the surgical laser to prevent thermal damage of the target tissue based on a signal from the infrared sensing assembly, such as reducing a power of the surgical laser when the infrared sensing assembly indicates that the temperature of the tissue reaches a warning level, or the rate of change of the temperature can show that the tissue can fast approach a damage threshold.

The surgical laser controller can be configured to measure temperature of the target tissue based on a signal from the infrared sensing assembly. The surgical laser controller can be configured to calculate a rate of change of a temperature of the tissue based on a signal from the infrared sensing assembly. For example, the upon predicting a potential damage conditions, the surgical laser controller can control at least a power, a pulse rate, and a pulse width of the first laser to prevent damage to the tissue due to overheating.

The surgical laser assembly can be configured to perform measurements during off-time of laser pulses of the first laser, e.g., the surgical laser controller can perform the measurements, such as fluorescent measurements, infrared measurements, Raman measurements, and near infrared measurements when the surgical laser is off.

To increase the time for measurements, the surgical laser controller can be configured to increase the off-time of laser pulses of the surgical laser by reducing the laser pulse widths when decreasing a power of the surgical laser. For example, if an average of 75 W laser power is needed, the power of each laser pulse can be set at 300 Watts, with a duty cycle of ¼ or 0.25%. The duty cycle can be defined as the ratio of the laser on-time over the period of the laser pulses. For example, a duty cycle of ¼ means that the laser is on for ¼ of the time. If the laser pulse has a period of 1 millisecond, the on-time of the laser is ¼ of a millisecond, or 0.25 millisecond. Thus, the surgical laser controller can be configured to maximize the off-time of the laser pulses of the surgical laser by maintaining a constant peak power of each laser pulse while changing the laser pulse widths (or duty cycle). For example, to increase a power from 75 W to 100 W, the maximum power of the surgical laser can still be set at 300 W, and the duty cycle can increase from 25% to 30%.

The surgical laser controller can be configured to change a power of the laser by discretely changing peak power per pulse while continuously changing a duty cycle between pulses.

In some embodiments, the surgical laser assembly can be configured to have a duty cycle of laser pulses less than or equal to 10% for most or all power settings, e.g., a maximum duty cycle value of 10%. The low values of duty cycle can provide a long off-time of the surgical laser, which can provide a long time for the measurement processes without being interfered by the surgical laser pulses. The low values of the duty cycle can be achieved by setting a high maximum power level. For example, to obtain 50 W at 10% duty cycle, the maximum power of each laser pulse can be set at 500 W. Other maximum duty cycle values can be used.

In some embodiments, the surgical laser can have a limit of maximum power, such as 100 Watts. The duty cycle then can be set at a maximum value with the power set at the maximum value.

For example, to achieve 20 Watts average power, the duty cycle is at 20%. To achieve 50 Watts of power, the maximum duty cycle is at 50%.

In some embodiments, the present invention discloses a robotic device for surgical operations. The robotic device can include a robot, a surgical laser assembly coupled to the robot, an optical assembly, an aiming laser assembly, a fluorescent sensing assembly, an infrared sensing assembly, and a controller.

In some embodiments, the present invention discloses a method to operate a surgical laser assembly. The method can include using an aiming laser to provide excitation energy to tissues to emit a fluorescent signal, and then using the fluorescent signal to control a surgical laser for operating on the tissues. The method can also include detecting infrared signals from tissues to determine a temperature or a rate of temperature of the tissues to control a power, a pulse rate, or a pulse width of the surgical laser to prevent thermal damage to the tissues. The method can further include setting a power of the surgical laser to maximum levels with power changing is achieved by changing laser pulse width of the surgical laser to increase off-time of the surgical laser for data collection.

BRIEF DESCRIPTION OF THE DRAWINGS

FIGS. 4A-4B illustrate flow charts for forming surgical laser systems with tissue identification capability according to some embodiments.

FIGS. 5A-5C illustrate flow charts for operating a surgical laser system with tissue identification capability according to some embodiments.

FIGS. 8A-8D illustrate configurations of surgical laser systems according to some embodiments.

FIG. 12A-12C illustrate flow charts for operating a surgical laser system having a thermal tracking capability according to some embodiments.

DETAILED DESCRIPTION OF THE EMBODIMENTS

The present invention relates to surgical laser systems, and methods to operate the surgical laser systems, with sensors, such as temperature and tissue sensors, to optimize laser delivery settings for target the desired tissues and cut down surgical times.

In some embodiments, the present invention discloses a surgical laser system, and methods forming and operating the surgical laser system, that has a capability of detecting fluorescence of the operated-upon tissue. Tissue can include molecules connected or weaved together, such as fat molecules, proteins molecules, DNA molecules. Water and lipids are two elements dominant in human tissues. The tissue can be excited by the aiming laser of the surgical laser system, either by auto-fluorescent or by using a fluorescent dye previously administered to the patient. Spectral fluorescent signal can also be collected, using multiple frequency aiming laser, such as multiple aiming lasers having difference colors, or an aiming laser assembly having variable frequencies. The detected fluorescent signal can assist the surgical process, for example, by identifying the tissue, such as tissue types, hard or soft tissues, and other characteristics relevant to the operation of the surgical laser.

The surgical laser system, with its sensing capability, can serve as a diagnostic tool for tissue pathology, stone composition, cancerous or precancerous tissue precaution and warning. As a result, the right laser power, laser pulse setting or mode can be delivered to the target tissue during surgery to improve efficacy of treatment. The surgical laser system can provide minimally invasive procedures, and also can provide data via its sensing capability to significantly improve the safety and efficacy of the surgical procedures, together with reducing OR (Operating Room) time and hospital stay. In addition, the surgical laser system can be coupled to a robotic system to provide a full operation suite to the surgeon.

Figure 1A:
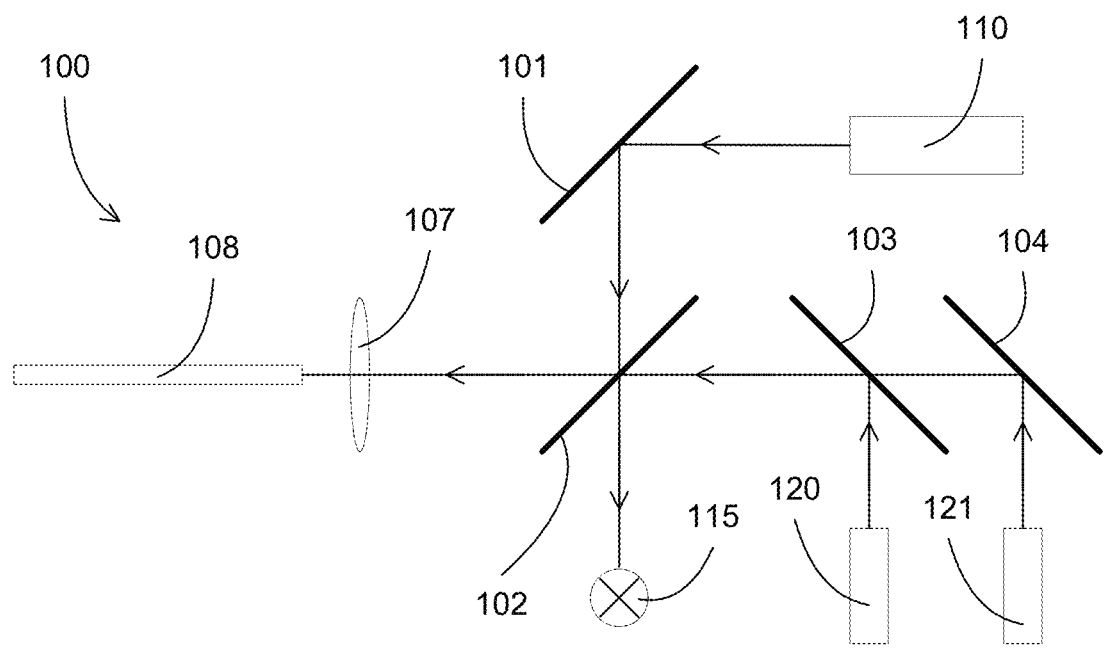
FIGS. 1A-1B illustrate prior art surgical laser systems according to some embodiments.
Figure 1B:
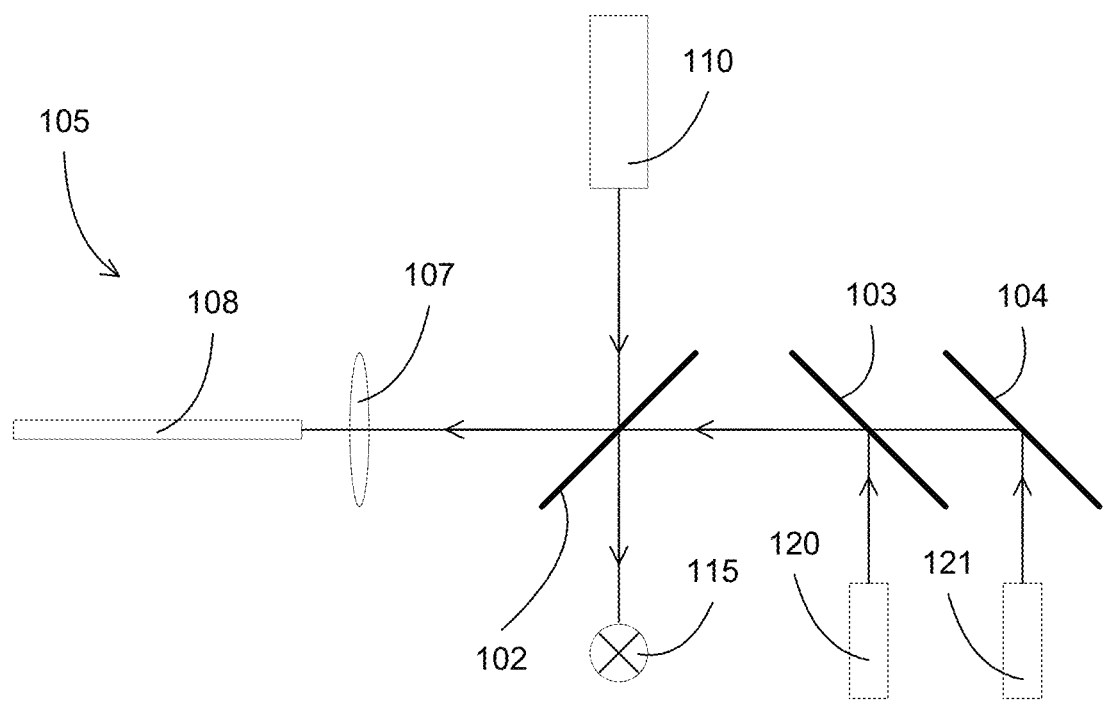
Figure 2:
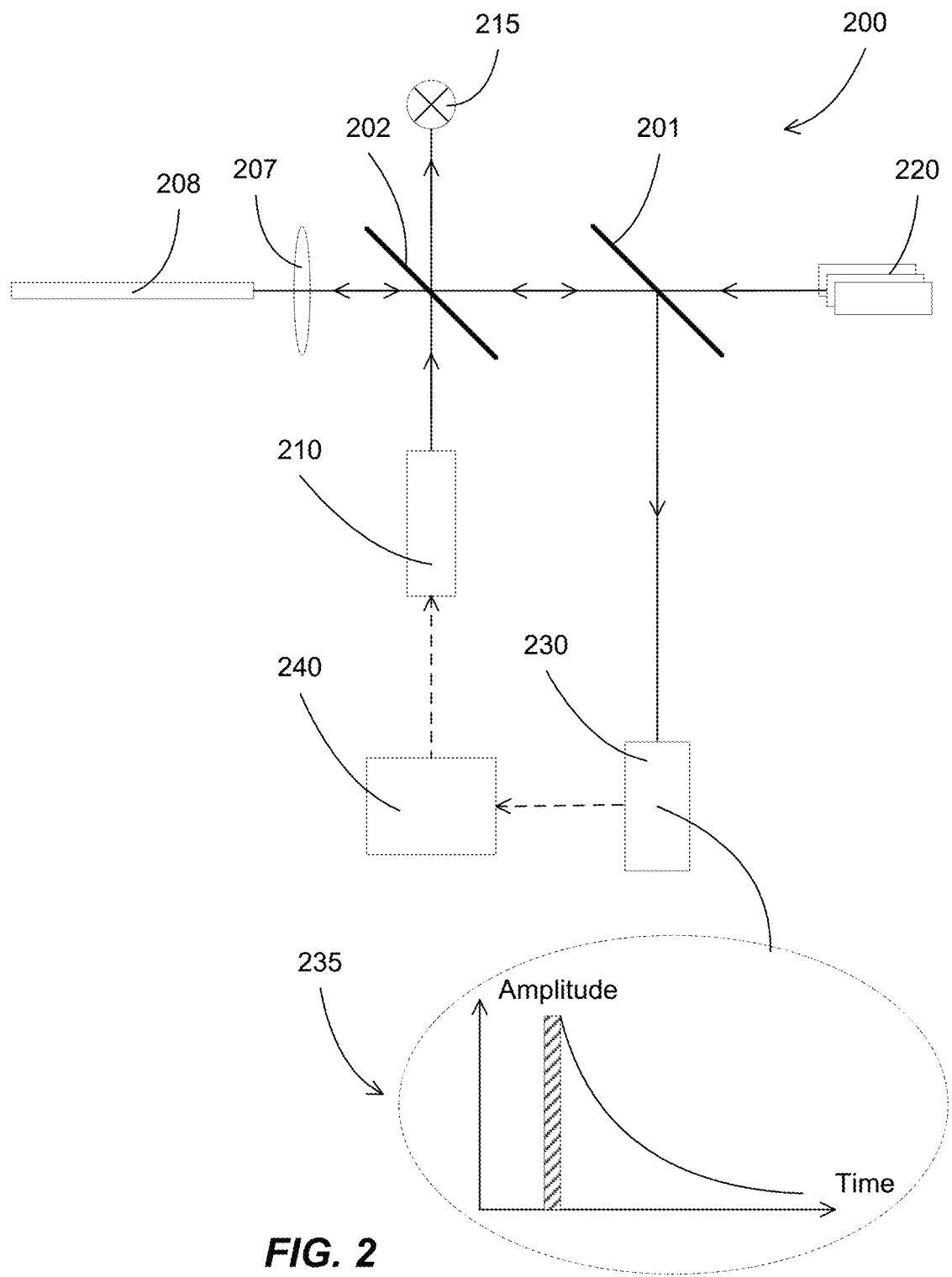
FIG. 2 illustrates a surgical laser system having a fluorescent capability according to some embodiments.

FIG. 2 illustrates a surgical laser system having a fluorescent capability according to some embodiments. The fluorescent-detection surgical laser system can be used to identify tissues, which can assist the surgical process, such as assisting the surgeon in determining operating conditions for the surgical laser for the tissue currently being operated on.

A surgical laser system having a tissue identification capability through fluorescent signal can include components of a conventional surgical laser system, together with a fluorescent sensor assembly and a controller capable of processing the fluorescent signal collected by the fluorescent sensor assembly, together with feedback to control the surgical laser and optionally to the aiming lasers.

The surgical laser system 200 can include a surgical laser 210, which can be a laser having wavelengths appropriate to the surgical operation, such as 1470-2100 nm. The surgical laser can be configured for water and lipid absorption using wavelength in the range from 1470 nm to 2100 nm, such as 1470 nm wavelength lasers.

The surgical laser system 200 can include an optical assembly to bring the output of the surgical laser 210 to an optical fiber 208, the distal end of which can be inserted inside a patient for surgical operations, such as tissue cutting or ablating. The optical assembly can include a beam splitter 201, which can direct the output of the surgical laser to the optical fiber 208 and also to an internal energy sensor 215 for measuring the output power of the surgical laser. The internal energy sensor can include standard InGaAs sensor, for example, for the 1470 nm surgical laser, and extended InGaAs sensor for longer wavelengths. The laser energy detector can be sensitive from 1.0 um to 1.6 um range for the 1470 nm laser.

The optical assembly can include an output lens 207 for focusing the laser beam emitted from the surgical laser. The optical assembly can also include other components, such as a laser beam guiding assembly for guiding the laser beam.

The surgical laser system can include an aiming laser assembly 220, which can reach the beam splitter 201 to merge with the surgical laser. The aiming laser assembly 220 can include a single laser to provide single frequency aiming laser, such as a blue laser having wavelengths of 365-440 nm. The aiming laser assembly 220 can include a laser assembly capable of providing laser beams having multiple frequencies, such as a blue laser and a green laser having wavelengths of 535±20 nm, or a blue laser having wavelength of 365 nm to 470 nm, a green laser, and a red laser having wavelengths of 635±20 nm.

The aiming laser can include laser beams in visible spectrum, such as blue, green, and red lasers or in the invisible ultraviolet. The aiming laser assembly can be controlled by a user, such as controlling the aiming beam color and/or intensity via a touch screen by a surgeon during the surgical operation. The aiming laser assembly can be used to track position of the target, together with other functions such as providing warning or marking references. For example, the green aiming laser can be used for tracking tissue position. The red aiming laser can also be used for tracking tissue position, together with additional functions such as flickering when needed to give the surgeon a warning, and marking references for robotic assisted surgery device.

The surgical laser system 200 can further include a fluorescent detection assembly 230, which can include a fluorescent sensor together with support circuitries. A second beam splitter 202 can be included and disposed in the laser path, to provide inputs to the fluorescent detection assembly.

Upon excitation by the aiming laser 220, the tissue can emit fluorescent radiation, for example, by auto-fluorescent mechanism due to the tissue characteristics or by a fluorescent dye previously provided to the tissue. The fluorescent detection assembly can receive the emitted fluorescent signal, such as measuring the temporal relation of the emitted fluorescent signal 235, e.g., the amplitudes of the fluorescent signal together with the decay curve of the fluorescent signal. For example, a blue aiming laser can serve as an excitation light pulse source to excite tissue to stimulate tissue fluorescent during ablation or enucleation tissue, especially when removing tissue down to the prostate capsule, near the blood vessels, or cancerous tissues.

The collected fluorescent signal can be sent to a controller 240 for processing, such as to determine the characteristics of the tissue aimed at by the aiming laser, including the identification of the tissue. The information can be displayed, for example, on a screen, to assist the surgeon in making decisions on the tissue operation. Alternatively or simultaneously, the information can be sent to the surgical laser to set an operating condition of the surgical laser that is appropriate to the detected tissue, or to limit an operating condition of the surgical laser based on the detected tissue to prevent damage to the tissue.

In some embodiments, the fluorescent process can be an auto-fluorescent process, e.g., the natural emission of light by the tissue when absorbing light from the aiming laser. The emitted fluorescent signal can depend on the tissue, thus a detection of the fluorescent signal can allow a determination of the tissue characteristics, such as the identification of the cancerous tissue. For example, auto-fluorescent from the tissue can provide input to a robotic device in control surgery or biopsy processes.

In some embodiments, the fluorescent process can be caused by artificially added fluorescent dyes or markers, such as imaging agents or dyes. The dye can be injected according to the surgeon prescription, for example, to assist in the detection and monitoring of precancerous and cancerous tissue during surgery, such as to provide detailed images of the cancerous tissues and blood supply to the tumor.

With active fluorescent images, a surgeon can see below the surface of the tissue, for example, using an imaging method appropriate for the injectable fluorescent dye during the surgery, such as during a robot-assisted surgery. Using the robotic system, a high resolution or 3-D image of the target tissue with added fluorescent signatures will help to verify cancerous versus healthy tissue. The fluorescent imaging would help to eliminate the risk of leaving more cancerous tissue in the margin of the tumor after surgery. Further, with the target tissue image delineating the healthy and cancerous tissues, the surgeon can remove tumors with better safety margin, less blood loss, scarring, and minimum post-op pain or irritation.

Figure 3:
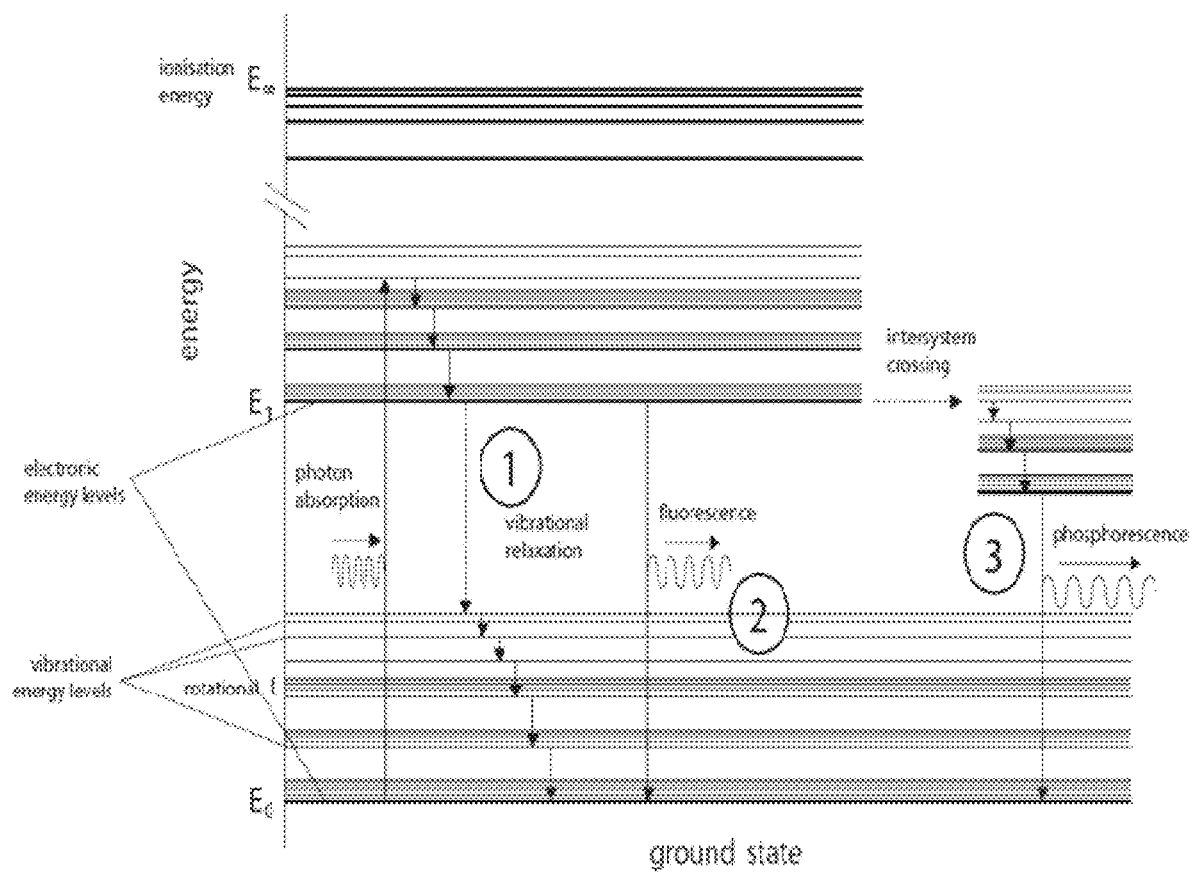
FIG. 3 illustrates a fluorescent mechanism viewed by energy levels of quantum physics.

FIG. 3 illustrates a fluorescent mechanism viewed by energy levels of quantum physics. A tissue or a fluorescent dye, e.g., marker, can absorbed photon energy, such as from the blue aiming laser, to transition to an excited state. The excited tissue or a fluorescent dye can decay by various radiative and non-radiative processes before emitting a fluorescent signal to return to the ground state.

By detecting the emitted fluorescent signal, the decay life time of the tissue or a fluorescent dye can be observed. The fluorescent lifetime can be an important parameter in determining the characteristics of the tissue, such as the identification of the tissue to determine whether or not the tissue is a cancerous cell.

FIGS. 4A-4B illustrate flow charts for forming surgical laser systems with tissue identification capability according to some embodiments. A surgical laser system can include a surgical laser, together with a fluorescent sensor and a controller to process the fluorescent signal.

In FIG. 4A, operation 400 forms a surgical laser system. The surgical laser system can include a surgical laser, an aiming laser assembly, a fluorescent sensor, and a controller coupling an output of the fluorescent sensor to the surgical sensor. Visible light, such as laser diode or superluminescent (SLED) light, can serve as aiming beam and tracking, including lights having wavelengths of 532 nm±20 nm (green color), 635 nm±20 nm (red color), and 365-440 nm (blue color). Other color aiming lasers can be used.

The aiming laser assembly can be configured to excite tissue to stimulate tissue fluorescence that can be detected by the fluorescent sensor. For example, the aiming laser assembly can include a blue laser having wavelengths between 365 and 440 nm, which can have high enough energy to excite tissues. The aiming laser is already aimed at the tissues to be operated on, thus the use of the aiming laser to excite the tissue can be automatic, e.g., the tissue can already be excited when the aiming laser points at the tissue. In some embodiments, the intensity, the pulse width, and the wavelengths of the aiming laser are selected to provide fluorescent signals suitable for tissue identification.

The aiming laser assembly can provide lights having a single frequency or multiple frequencies. For example, a single blue aiming laser can be used, serving as an aiming laser together with exciting the tissue to undergo fluorescent radiating process. Alternatively, multiple color aiming lasers can be used, such as three color aiming laser systems of a blue laser, a green laser and a red laser. Multiple frequency exciting aiming laser assembly can provide more information about the tissue, such as a spectral response of the tissue, or different decay lifetime curves generated by different energy levels of the aiming laser assembly. For example, green and blue lights can diffuse and excite tissues differently, providing additional information about the tissue. In addition, three-color aiming beam designs can also serve as guiding target and tracking surgical position of different texture color surface on the target tissue, which can add precision and safety during the surgical procedures The fluorescent sensor can include a photodetector or a photomultiplier tube (PMT) to detect the fluorescent signal. Other components can be included, such as optical filters to separate the emission wavelengths from others, such as from the excitation, e.g., the aiming laser, and the surgical laser wavelengths.

In some embodiments, a spectral fluorescent sensor, such as hyperspectral sensor or multispectral sensor, can be used. The hyperspectral sensor can sense the wavelength of the emitted photons from the tissue. The hyperspectral sensor can have spectral resolutions to identify tissues, such as color filter array (CFA) of 16 bands of light of each pixel group and high gain bandwidth product, including sensor responding times in micro ($10^{-6}$) and nano ($10^{-9}$) second time scale.

The spectral fluorescent sensor can include a multi-channel spectroscopy system with high spectral resolution, and high spatial differentiation. Further, a user can select spectral bands or wavelengths of interest. The spectral sensor can provide ease of tissue identification based on the spectral signatures of the tissue, for example, from an established library of known spectral signatures.

The controller can be configured to use fluorescent data from the fluorescent sensor to determine characteristics of the tissue, such as to identify the tissue as a healthy tissue or a cancerous tissue. The tissue characteristics can be presented to the surgeon, or can be used to control the surgical laser, such as to set or limit appropriate parameters of the laser for the detected tissue.

In some embodiments, the surgical laser system can be incorporated in a robotic device that can be capable of performing the surgical procedures. The controller can send the processed fluorescent data, e.g., the tissue characteristics, to assist the robotic device in the surgery.

Other components can be included in the surgical laser system, such as a Raman sensor to assist in the identification of tissue such as sensors to monitor tissue conditions (hard and soft tissue), and a near infrared camera for thermal tracking.

In FIG. 4B, operation 420 forms a surgical laser system having a controller for controlling operating conditions of the surgical laser. For example, the controller can control the power, and the pulse width of the surgical laser.

Operation 430 couples a fluorescent sensor to the surgical laser system. The fluorescent sensor can be configured to detect a fluorescent signal emitted by an element excited by an aiming laser of the surgical laser system. The fluorescent signal can be an auto-fluorescent signal, which is emitted by a tissue that is excited by the aiming laser. The fluorescent signal can be a stimulated emission light, which is emitted by a fluorescent dye that is injected to the tissue prior to the surgical operation. The fluorescent dye can be excited by the aiming laser. In some embodiments, the fluorescent sensor can be a spectral sensor, e.g., having a multi-channel spectroscopy system for detecting fluorescent signal in multiple frequency bands Operation 440 configures the controller for processing an output of the fluorescent sensor to determine characteristics of the tissue. The characteristics of the tissue can be configured to assist the controller in determining at least an operating condition of the surgical laser, such as a power of the laser, a pulse width of the laser, or an operation time of the laser. The controller can be configured to process the fluorescent sensor output to determine characteristics of the tissue to control the surgical laser.

FIGS. 5A-5C illustrate flow charts for operating a surgical laser system with tissue identification capability according to some embodiments. An aiming laser of the surgical laser system can excite the tissue to undergo auto-fluorescence or can excite a fluorescent dye in the tissue to undergo fluorescence. The fluorescent signal can be detected by a fluorescent sensor, either a single channel sensor or a multiple channel spectroscopy system. The detected fluorescent sensor can be processed by a controller, for example, to determine the lifetime decay of the fluorescent signal. The results can be used to assist the surgeon or the robotic device in operating the surgical laser. The feedback from the fluorescent data can provide a surgery having highest efficacy using the least laser power in the shortest time In FIG. 5A, operation 500 uses an aiming laser of a surgical laser system to excite tissue or the fluorescent dye in the tissue that is aimed at by the aiming laser. The excited tissue or dye can be configured to undergo fluorescent emission. The fluorescent emission can be configured to optimize a surgical laser system for the tissue.

In FIG. 5B, operation 520 uses detected fluorescent emission from tissue to optimize a surgical laser system for the tissue. The tissue or the dye in the tissue can be excited by an aiming laser of the surgical laser system.

In FIG. 5C, operation 540 aims at a tissue using an aiming laser of a surgical laser system. The aiming laser also excites the tissue to stimulate a tissue fluorescent process. Operation 550 detects fluorescent signal emitted by the tissue or by the dye. Operation 560 optimizes the surgical laser system for operating on the tissue based on the detected fluorescent signal.

In some embodiments, the surgical laser system can include three or more aiming laser beams in the visible spectrum. For example, the aiming lasers can include a blue aiming laser, a green aiming laser, and a red aiming laser. The aiming lasers can be mutually exclusive, e.g., each color aiming laser can be selected. The aiming lasers can be mixed, e.g., a combination of the three colors can be generated through a controller. The controller can determine the ratios of the three colors, together with the laser intensity or pulse width of each color.

Figure 6A:
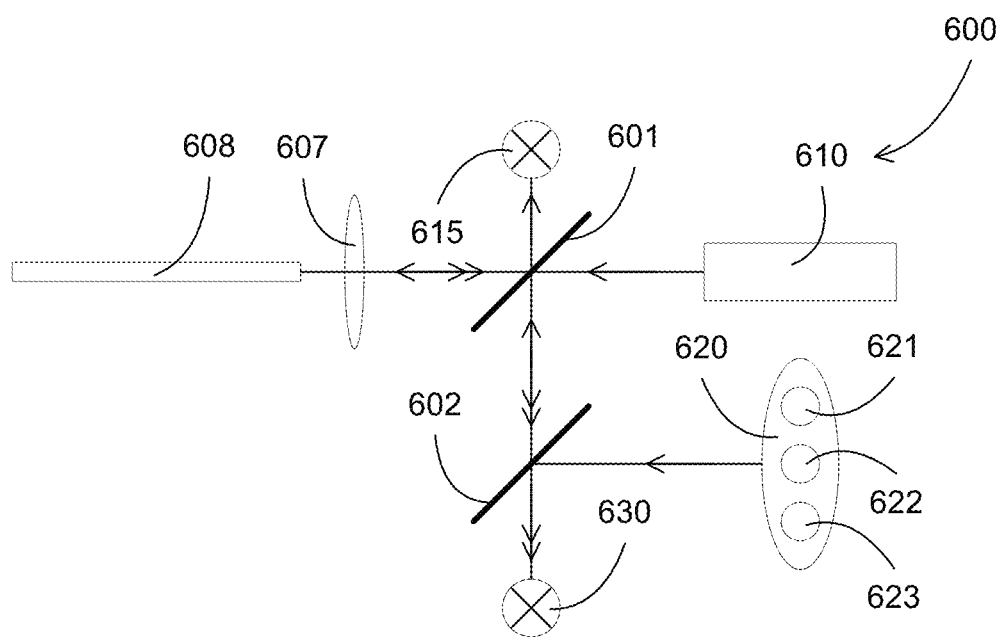
FIGS. 6A-6B illustrate configurations for multiple aiming lasers according to some embodiments.
Figure 6B:
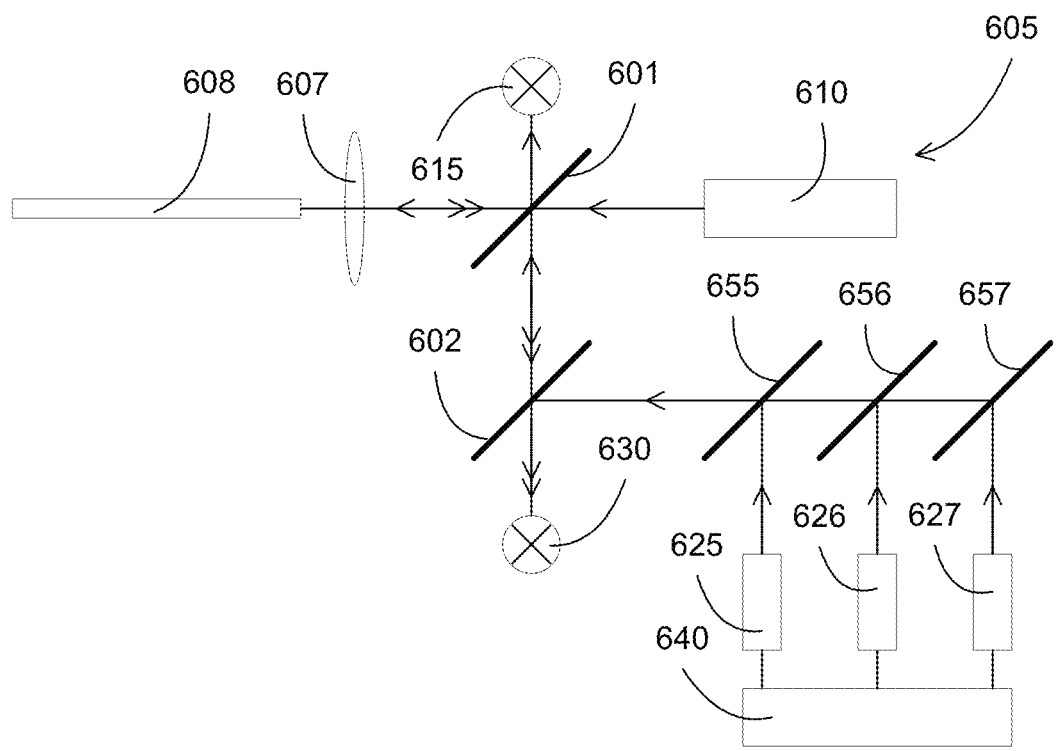

FIGS. 6A-6B illustrate configurations for multiple aiming lasers according to some embodiments. The aiming lasers can be selected by a rotating motor, or by an optical guiding assembly. In FIG. 6A, the aiming lasers 621, 622, and 623 of a surgical laser system 600 can be mounted on a rotating disc 620, which is controlled by a motor, such as a stepper motor for switching between different lasers. Three color lasers, such as low power (e.g., 1-100 mW power) laser diodes of blue, green and red, can be arranged with a stepper motor or a beam combiner. Three color lasers are shown, but other number of lasers can be used. Further, the mounting motor configuration can allow a selection of lasers, e.g., one color laser can be provided at one time by rotating the mounting disc. The outputs of the aiming lasers can merge with a surgical laser 610 through a combination of beam splitters 602 and 601, to reach an optical fiber 608 through an output lens 207.

Other configurations can be used, such as stationary aiming lasers with the rotating disc rotating a mirror to reflect the outputs of the aiming lasers 621-623 to the beam splitter 602. The surgical laser system can include other components, such as an internal energy sensor 615 for measuring the output power of the surgical laser, a fluorescent detection assembly 630 to measure fluorescent signal emitted from the tissue, and a controller to control the aiming lasers and the motor.

FIG. 6B shows a configuration that can allow a selection of aiming lasers, together with a mixing of the outputs of the aiming lasers. An optical configuration including beam splitters 655, 656, and 657 can guide the aiming lasers 625, 626, and 627 of a surgical laser system 605 to merge with the surgical laser 610. A controller 640 can be included, which can control power, pulse width and intensity of the aiming lasers. By controlling the powers of the aiming lasers, any combination of the aiming lasers can be provided to the surgical laser system.

In some embodiments, the control of the aiming lasers can be through a touch screen. The aiming lasers can be continuous or pulsed. Other configurations can be used, such as a more than three aiming lasers, or a variable wavelength aiming laser assembly that utilizes an optical configuration to change the wavelengths of the aiming lasers.

In some embodiments, the surgical laser system can include a fluorescent sensing assembly for measuring the fluorescent signal emitted from the tissue, e.g., due to the tissue auto-fluorescence or due to a fluorescent dye in the tissue. An optical path can be included from the tissue, e.g., from the optical fiber that brings the surgical and aiming lasers to the tissue, to a fluorescent sensor in the fluorescent sensing assembly. The fluorescent sensing assembly can be configured to obtain the emitted fluorescent signal as a function of time, e.g., measuring the fluorescent signal at different times to form a temporal relationship of the fluorescent signal. The curve of the fluorescent signal and time can allow a determination of instantaneous fluorescent intensities, together with rates of change of the fluorescent intensities with time.

In some embodiments, the fluorescent sensing assembly can provide a spectroscopic sensing capability, e.g., a hyper-spectral or multi-spectral fluorescent sensing assembly that can measure the fluorescent signal in both time and wavelength. The variations in time of the measured fluorescent signals can allow the calculation of lifetime decay of the fluorescent signal, which can be specific to the tissues and thus can provide a tissue identification and characterization. The variations in wavelength of the measured fluorescent signals can allow a better characterization of the tissue, including an identification of the tissue from a surgical point of view.

In some embodiments, the surgical laser system can include a controller to process the received fluorescent signal. The controller can also be configured to control the lasers, e.g., controlling the power, pulse width, or intensity of the surgical laser and the aiming lasers. Alternatively, separate controllers can be used to control the lasers. The controller can control the aiming lasers to form as excitation sources to excite the tissue (or the fluorescent dye), e.g., determining the wavelength, power, pulse width and/or intensity of the aiming lasers to be used to excite the tissue.

The controller can couple the fluorescent signal with the laser control, e.g., allowing a better control of the surgical laser with knowledge of the target tissue. For example, the measured fluorescent signal can provide indication that the tissue aimed at by the aiming lasers is a healthy or cancerous tissue, and thus can control the surgical laser to take appropriate actions.

Figure 7:
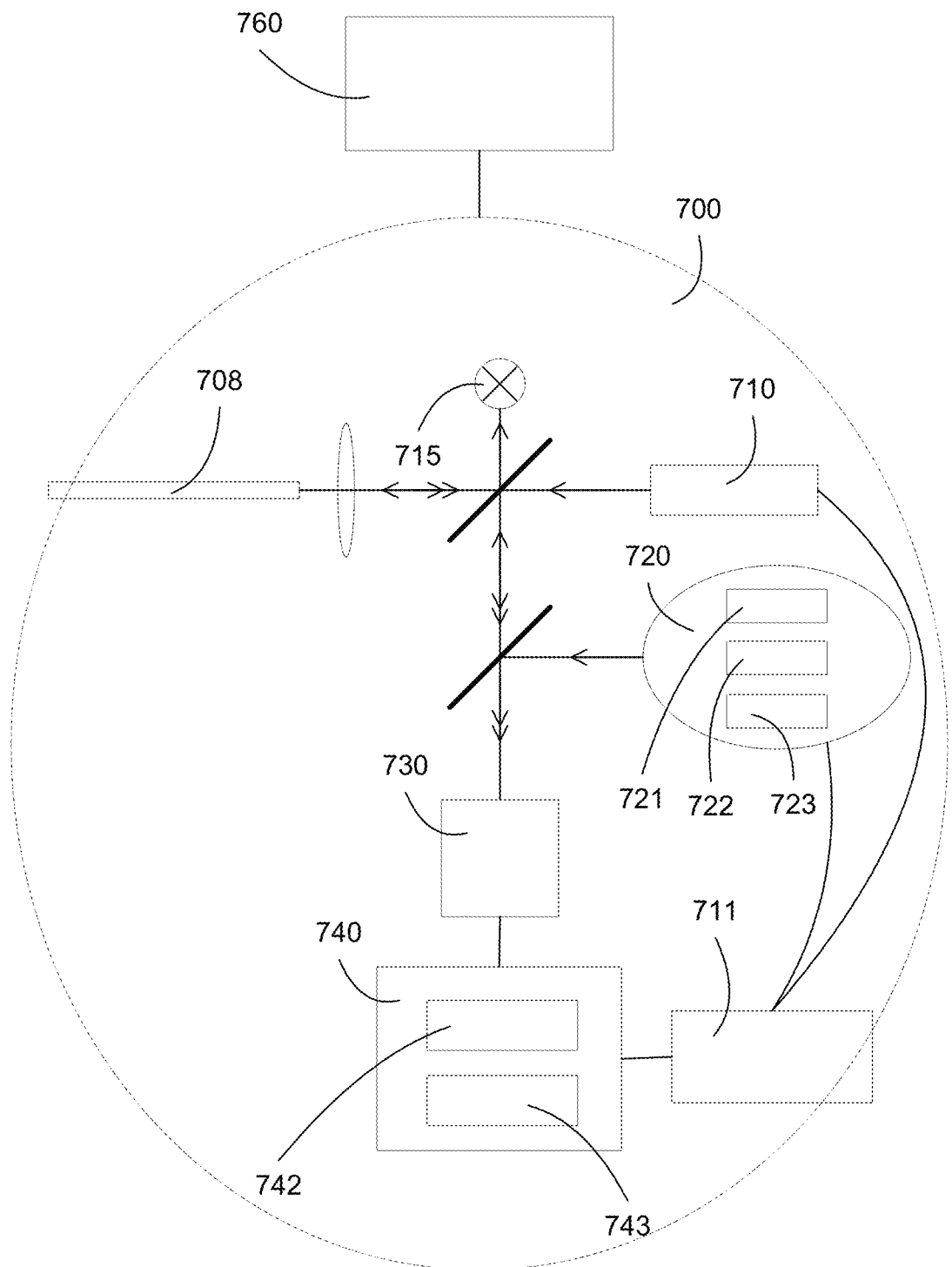
FIG. 7 illustrates a configuration of a surgical laser system according to some embodiments.

FIG. 7 illustrates a configuration of a surgical laser system according to some embodiments. A surgical laser system 700 can include a surgical laser 710 to provide a laser output to an optical fiber 708 through an optical guiding assembly. An internal sensor 715 can be included in the optical guiding path to measure the power of the surgical laser. A power supply 711 can be included to supply power to the surgical laser.

The surgical laser system 700 can include an aiming laser assembly 720, which can provide variable wavelength laser beam to the optical fiber 708, also through the optical guiding assembly. As shown, the aiming laser assembly can include 3 lasers 721, 722, and 723 of different wavelengths, such as a blue, a green, and a red color lasers. The aiming laser assembly can provide tracking and guiding the surgeon at the surgery location. The aiming laser assembly can also serve as excitation sources for exciting the tissue or the dye in the tissue to undergo fluorescent transition. The aiming laser assembly can be powered by a power supply, such as same power supply 711 that can powers the surgical laser.

The surgical laser system 700 can include a fluorescent sensing assembly 730, such as a mono-channel fluorescent sensor or a multi-channel fluorescent sensor (e.g., a spectrometer such as a hyperspectral or multi-spectral sensor). The fluorescent sensing assembly can receive signal from the tissue, for example, through the optical guiding assembly, to detect the fluorescent signal emitted from the tissue. Other components can be included, such as optical filters for filtering the signals.

The surgical laser system 700 can include one or more controllers 740 for processing the fluorescent signal and for controlling the lasers. The controllers can include a signal processing module 742 and a microcontroller 743 to process the data from the fluorescent sensing assembly. The controllers can communicate with the power supply 711 to use the processed fluorescent data to control the surgical laser and the aiming lasers.

The surgical laser system 700 can include other components, such as a display for displaying information from the lasers and from the sensor, together with an input module for controlling the surgical laser system. The surgical laser system can include other sensors for optimizing the operation of the lasers.

In some embodiments, the surgical laser system 700 can be configured to integrate with a surgical robotic system 760, to allow a robot surgery system or a robot-assisted surgery system. FIGS. 8A-8D illustrate configurations of surgical laser systems according to some embodiments.

In FIG. 8A, operation 800 forms a switching assembly for switching between different color aiming lasers of a surgical laser system having fluorescent characterization of tissue. The switching assembly can include a rotation assembly. For example, the switching assembly can include a rotating disc powered by a motor, such as a stepper motor for stepping between aiming lasers. The aiming lasers can be mounted on the rotating disc. The rotating disc can include optical assembly, such as mirrors, to guide the outputs from different aiming lasers.

In FIG. 8B, operation 820 forms a mixing assembly for mixing different color aiming lasers of a surgical laser system having fluorescent characterization of tissue. The mixing assembly can include an optical assembly for mixing the outputs of the aiming lasers. A controller can be included to control the ratios of the mixture, e.g., determining the percentages of different aiming lasers.

In FIG. 8C, operation 840 forms a spectral fluorescent sensing assembly for assessing fluorescent signal from a surgical laser system having multiple frequency aiming laser assembly. The spectral fluorescent sensing assembly can include a spectrometer such as a hyperspectral or multi-spectral sensor.

In FIG. 8D, operation 860 integrates a surgical laser system having multiple frequency aiming laser assembly to a surgical robotic system.

Figure 9A:
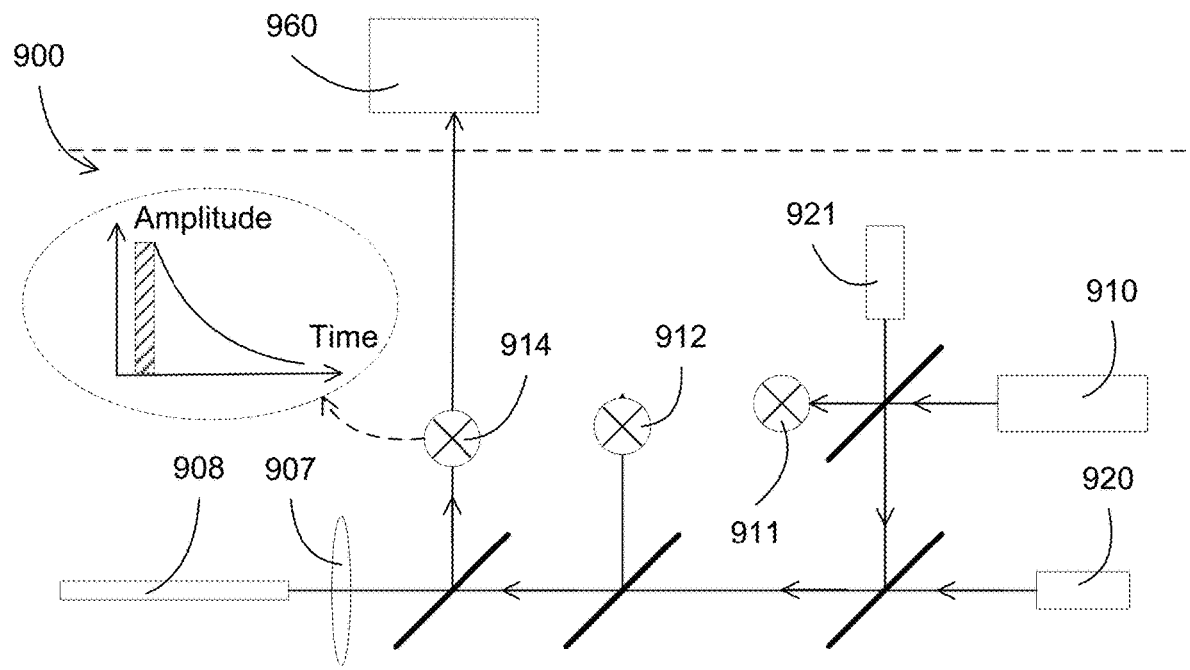
FIGS. 9A-9C illustrate configurations for a laser surgical system incorporating a fluorescent sensor according to some embodiments.
Figure 9B:
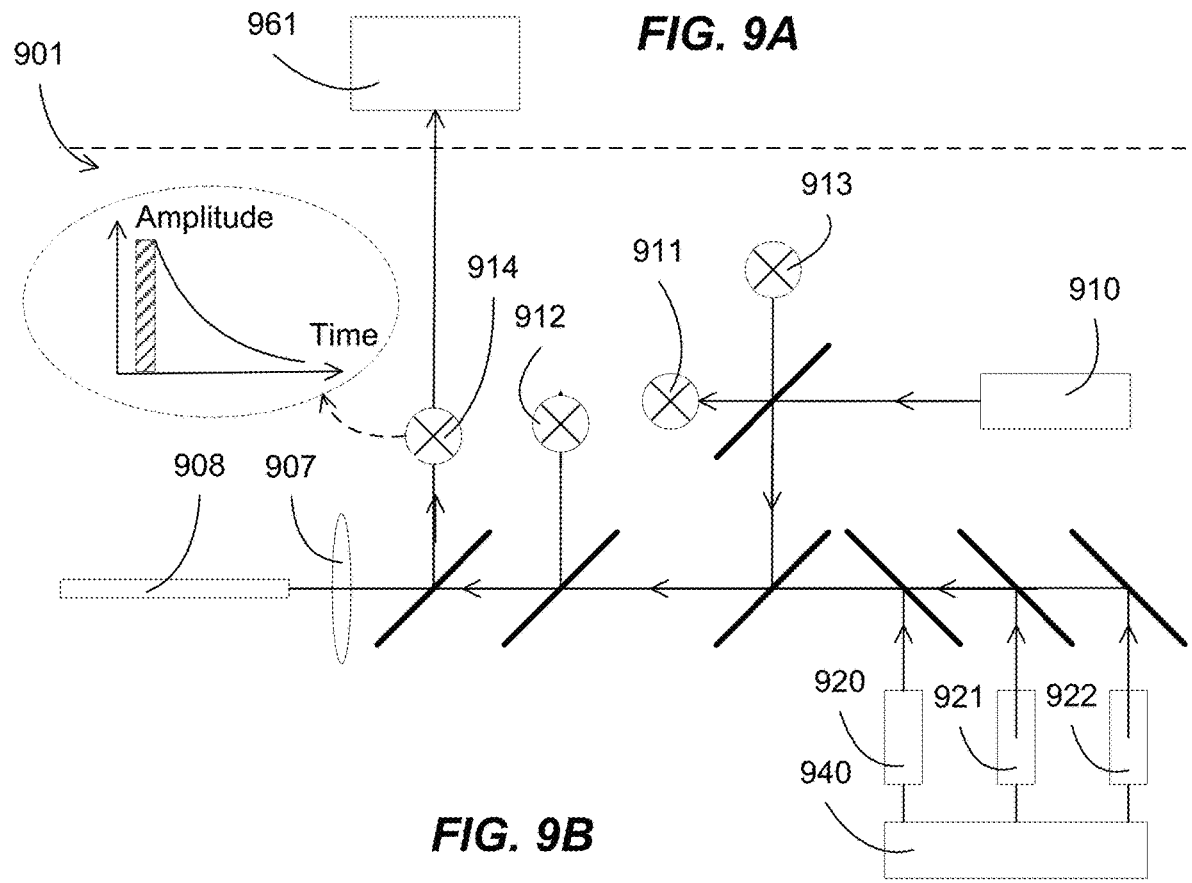
Figure 9C:
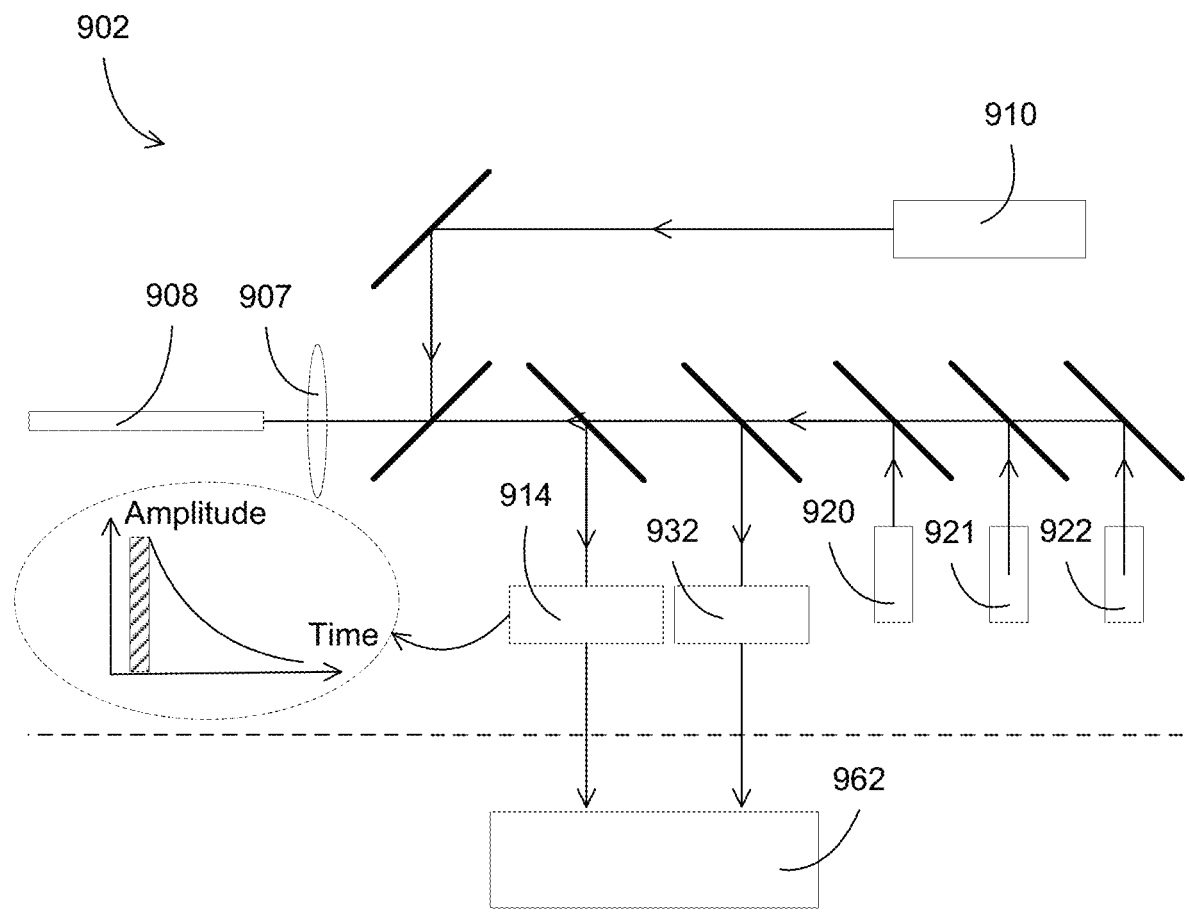

FIGS. 9A-9C illustrate configurations for a laser surgical system incorporating a fluorescent sensor according to some embodiments. The fluorescent signal from the tissue that is subjected to the surgery process can provide input, such as to the surgeon or to a robotic device in control surgery or biopsy processes, to assist in the surgery process.

In some embodiments, the aiming lasers can be used to provide the excitation source for the fluorescent decay from the tissue. Multiple wavelength aiming lasers, characterized by the different laser colors, such as red, blue and green lasers, can excite the tissue differently, to generate different fluorescent signals, e.g., different decay curves or different diffusion curves. The fluorescent behaviors of the tissue from different wavelengths can provide a spectral view of the tissue, which can assist in identify and clarify the tissue, such as the tissue types or tissue characteristics.

In some embodiments, the fluorescent process can be an auto-fluorescent process, e.g., the tissue can be excited by the aiming lasers to undergo fluorescent decay. Alternatively, the fluorescent signal can be generated by using fluorescent labeled markers, such as imaging agents, dyes, to detect and monitor precancerous and cancerous tissue during surgery. The marker can be injected if needed per surgeon prescription, to provide detailed images of the cancerous tissues and blood supply to the tumor. For example, using a new imaging method with an injectable fluorescent dye to provide active fluorescent images, surgeons can see below the surface of human tissue, for example, during robot-assisted surgeries. A high resolution or 3-D image of the target tissue with added fluorescent signatures can help to verify cancerous versus healthy tissue. The fluorescent imaging would help to eliminate the risk that cancerous tissue margin can remain on the tumor after surgery. The fluorescent images can assist the surgeon in removing tumors with better safety margin, less blood loss, scarring, and minimum post-op pain or irritation.

In some embodiments, the surgical laser system can be incorporated in a robotic device, which can provide better precision and control of the surfer process. For example, the aiming lasers can closely track the position and orientation of the surgical instrument. Three-dimensional tracking systems employing multiple imaging systems or signaling elements can be readily adapted to the surgical laser system.

In FIG. 9A, a surgical layer system 900 can include a design specifically for fluorescent detection connected to an external robotic device. The surgical laser system 900 can include a surgical laser 910, which can be a laser having wavelengths appropriate to the surgical operation, such as 1470-2100 nm. For example, the surgical laser can be configured for water and lipid absorption using wavelength of 1470 nm.

The surgical laser system 900 can include an optical assembly, including a lens 907, to bring the output of the surgical laser 910 to an optical fiber 908, the distal end of which can be inserted inside a patient for surgical operations. The optical assembly can include one or more beam splitter and mirror, which can direct the output of the surgical laser to the optical fiber 908. An internal energy sensor 911 can be included for measuring the output power of the surgical laser. The surgical laser system can include one or more aiming lasers, with a blue aiming laser 920 (365-440 nm) and a green aiming laser 921 (535±90 nm) shown, which can reach the optical assembly to merge with the surgical laser. Other aiming lasers with different wavelengths can be included, such as a red aiming laser.

The surgical laser system 900 can further include a fluorescent detection assembly 914, which can include a fluorescent sensor together with support circuitries. The optical assembly can include a path for the fluorescent signal from the tissue to travel through the optical fiber 908 to reach the fluorescent detection assembly 914.

Upon excitation by the aiming lasers, the tissue can emit fluorescent radiation, for example, by auto-fluorescent mechanism due to the tissue characteristics or by a fluorescent dye previously provided to the tissue. The fluorescent detection assembly can receive the emitted fluorescent signal, which can be sent to an external robotic device or system 960 for controlling the movements of the surgical laser system, including controlling the characteristics of the surgical laser and the aiming lasers.

In some embodiments, the surgical laser system 900 can further include an infrared detection assembly 912, such as an infrared tissue temperature sensor capable of detecting short wavelength infrared (between 1.7 and 2.2 micrometer). The infrared sensor can monitor the temperature of the tissue, for example, to prevent damage to the tissue by laser heating. Infrared signal or infrared images can be collected for determining the tissue temperature.

In FIG. 9B, a surgical laser system 901 can include a design with no-moving 3-color aiming beams, and a fluorescent detection sensor for cancerous and precancerous tissues. The surgical laser system 901 can include a surgical laser 910, which can be a laser having wavelengths appropriate to the surgical operation. The surgical laser system 901 can include an optical assembly, including a lens 907, to bring the output of the surgical laser 910 to an optical fiber 908, the distal end of which can be inserted inside a patient for surgical operations. The optical assembly can include one or more beam splitter and mirror, which can direct the output of the surgical laser to the optical fiber 908. An internal energy sensor 911 can be included for measuring the output power of the surgical laser.

The surgical laser system can include one or more aiming lasers, with a blue aiming laser 920 (365-440 nm), a green aiming laser 921 (535±90 nm), and a red aiming laser 922 (635±20 nm) shown, which can reach the optical assembly to merge with the surgical laser. The aiming lasers can be controlled by a microprocessor system 940, such as to control powers and pulse widths of the aiming lasers. The microprocessor system can also operate to select the aiming lasers to provide to the optical fiber, e.g., turning on the blue aiming laser and turning off the green and red aiming laser. This configuration can serve to excite the tissue with the blue wavelength laser for the fluorescent detector to detect fluorescent signal excited by radiation having wavelengths of 365-440 nm. The microprocessor system can also operate to control the aiming lasers with appropriate Other aiming lasers with different wavelengths can be included.

The surgical laser system 901 can further include a fluorescent detection assembly 914, which can include a fluorescent sensor together with support circuitries. The optical assembly can include a path for the fluorescent signal from the tissue to travel through the optical fiber 908 to reach the fluorescent detection assembly 914.

Upon excitation by the aiming lasers, the tissue can emit fluorescent radiation, for example, by auto-fluorescent mechanism due to the tissue characteristics or by a fluorescent dye previously provided to the tissue. The fluorescent detection assembly can receive the emitted fluorescent signal, which can be sent to an external robotic device or system 961 for controlling the movements of the surgical laser system, including controlling the characteristics of the surgical laser and the aiming lasers.

In some embodiments, the surgical laser system 901 can further include an infrared detection assembly 912, such as an infrared tissue temperature sensor capable of detecting short wavelength infrared (between 1.7 and 2.2 micrometer). The infrared sensor can monitor the temperature of the tissue, for example, to prevent damage to the tissue by laser heating. Infrared signal or infrared images can be collected for determining the tissue temperature.

In some embodiments, the surgical laser system 901 can further include a fiber protection sensor, which can detect abnormal conditions to the optical fiber tip, such as overheating.

In FIG. 9C, a surgical laser system 902 can include an optical path arrangement for three color aiming beam plus tissue fluorescent detection. The surgical laser system 902 can include a surgical laser 910, which can be a laser having wavelengths appropriate to the surgical operation. The surgical laser system 902 can include an optical assembly, including a lens 907, to bring the output of the surgical laser 910 to an optical fiber 908, the distal end of which can be inserted inside a patient for surgical operations. The optical assembly can include one or more beam splitter and mirror, which can direct the output of the surgical laser to the optical fiber 908.

The surgical laser system can include one or more aiming lasers, with a blue aiming laser 920 (365-440 nm), a green aiming laser 921 (535±90 nm), and a red aiming laser 922 (635±20 nm) shown, which can reach the optical assembly to merge with the surgical laser.

The surgical laser system 902 can further include a fluorescent detection assembly 914, which can include a fluorescent sensor together with support circuitries. The optical assembly can include a path for the fluorescent signal from the tissue to travel through the optical fiber 908 to reach the fluorescent detection assembly 914.

Upon excitation by the aiming lasers, the tissue can emit fluorescent radiation, for example, by auto-fluorescent mechanism due to the tissue characteristics or by a fluorescent dye previously provided to the tissue. The fluorescent detection assembly can receive the emitted fluorescent signal, which can be sent to an external robotic device or system 962 for controlling the movements of the surgical laser system, including controlling the characteristics of the surgical laser and the aiming lasers.

In some embodiments, the surgical laser system 902 can further include an assembly 932 for detecting other characteristics of the tissue, such as a near IR spectrometer and a Raman spectrometer. A photomultiplier can be included for amplifying the detection signals.

Other components can be included, such as an internal energy sensor for measuring the output power of the surgical laser, a control system for controlling the aiming lasers, aiming lasers with different wavelengths, an infrared tissue temperature sensor for monitoring the temperature of the tissue, and a fiber protection sensor for protecting the optical fiber.

In some embodiments, the present invention discloses a surgical laser system, and methods forming and operating the surgical laser system, that can minimize thermal damages to the tissue undergoing the surgical operation. The surgical laser system can include a thermal sensing assembly for monitoring the temperature and the temperature rates of change of the tissue. The surgical laser system can use the sensed thermal information to control the surgical laser to prevent the tissue to exceed the temperatures that can cause irreversible damages to the tissue. The irreversible damage temperatures can be a function of exposure time, thus the surgical laser system can also keep track of the laser time to determine the proper critical temperatures. Further, the rates of change of the tissue temperature can allow a prediction of the tissue temperature based on the settings of the surgical laser, which can allow the surgical laser to operate near the critical temperature without the possibility of exceeding the critical temperature. The measured tissue temperature can serve as an end-point for the laser surgical procedures, together with improving safety and efficacy. For example, the tissue temperature can be regulated to be less than 60° C. to prevent hyperthermia, e.g., reactions of heat transfer to the tissue. The reactions can include collagen gelatinization and subsequently coagulation of the tissue, or the denaturation of cell membranes or cytoplasmic proteins leading to necrotic or apoptotic cell death. Coagulative necrosis is a type of accidental cell death typically caused by ischemia or infarction. It is characterized by a 'ghostly' appearance of cells under light microscopy in the affected area of tissue.

In some embodiments, the surgical laser system can be configured to provide a quantitative measure of the temperature of the target tissue. For example, this capability can be useful in laser liposuction, wound healing, tissue welding and cancer detection. An infrared detector or camera for detecting short wavelength infrared (around 1.7 microns), such as an In/GaAs sensor, can be mounted in the optical path from the optical fiber. Other types of infrared detectors that can be utilized include silicon, germanium and pyroelectric detectors. The infrared detector or camera can detect the temperature of the target tissue, for example, during periods that the laser source is switched off. The infrared tissue temperature sensor can be calibrated using a black body radiator (with emissivity of approximately 1) to create a look-up table to determine the temperature. For greater accuracy, a visible light camera can be used to produce a color image of the tissue being measured to estimate the emissivity of tissue.

In some embodiments, the surgical laser system can include tissue monitoring assembly, such as using a fluorescent sensing assembly as described above, together with other tissue sensing methods such as processing Raman signal emitted from the tissue to determine the tissue conditions. The identification of tissue can provide an accurate thermal tolerance of the tissue, which can allow the appropriate critical temperature that the tissue can accept before an irreversible damage, which can lead to lower surgical times.

Figure 10:
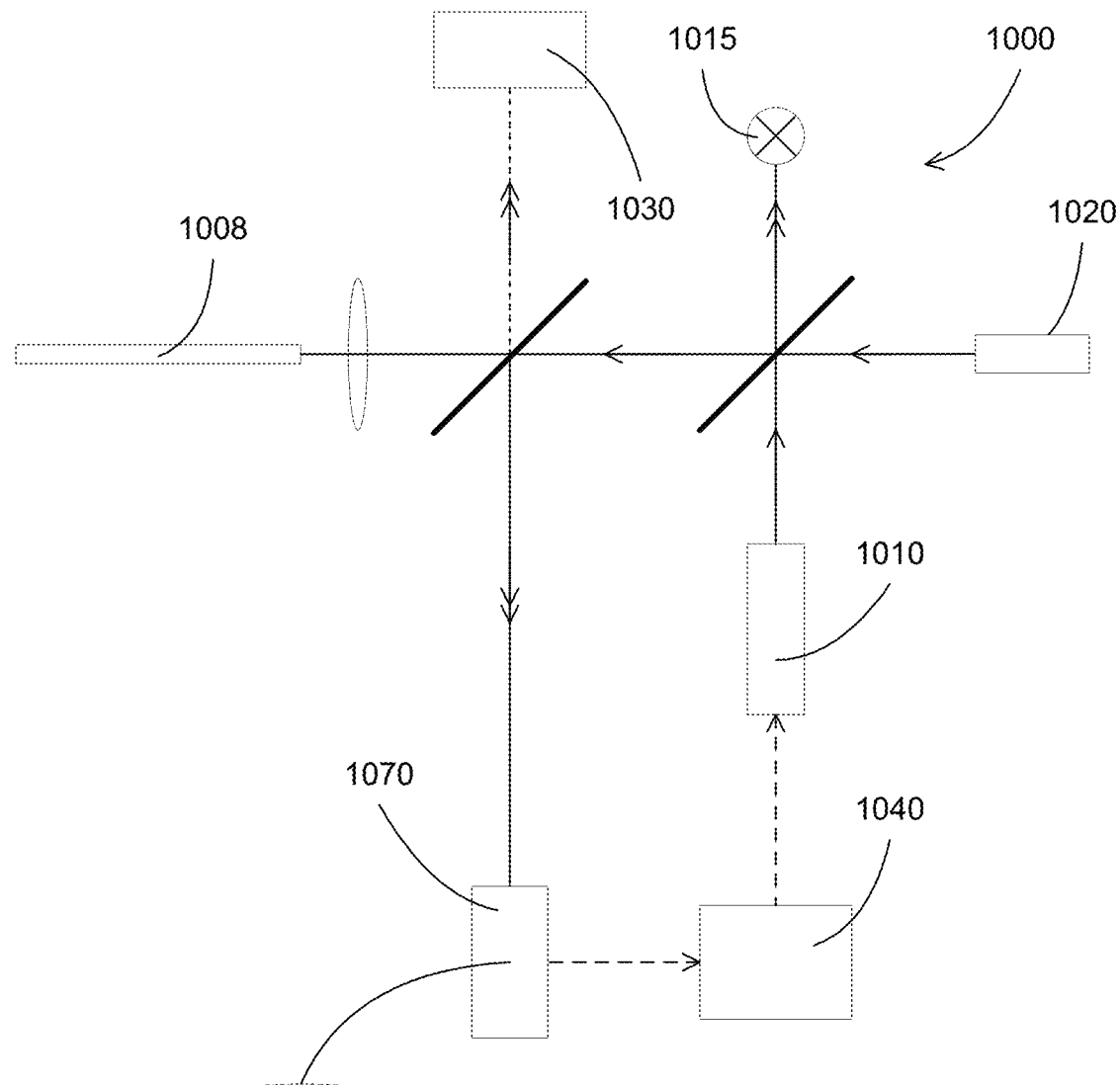
FIG. 10 illustrates a configuration for a surgical laser system having a thermal control according to some embodiments.

FIG. 10 illustrates a configuration for a surgical laser system having a thermal control according to some embodiments. A surgical laser system 1000 can include a surgical laser 1010 to provide a laser beam to an optical fiber 1008 through an optical guiding path assembly. An energy sensor 1015 can be coupled to the optical guiding path to measure the power of the surgical laser. An aiming laser assembly 1020 can be included, having outputs merged with the surgical laser at the optical fiber.

A temperature sensing assembly 1070 can be coupled to the optical guiding path to receive signals from the tissue through the optical fiber. The temperature sensing assembly can include infrared (IR) detector, such as pyrometers and infrared thermometers, for determining the tissue temperature. For example, visible light silicon detector and extended InGaAs detector, sensitive in 1.7 μm to 2.5 μm range can be used. The temperature sensing assembly can measure the temperature curve 1073, including the temperature 1071 and the rate of change 1072 of the temperature on the tissue after each laser pulse, which can have a temporal relationship to the laser pulse. The thermal tracking can also be performed by an infrared camera, which can provide spatial information about the temperature as a function of time.

Tissue can emit radiant energy, e.g., thermal radiation as a result of the temperature of the tissue. The temperature of the tissue can be calculated from the Stefan-Boltzmann law, using black body radiation estimation, relating the measured thermal radiation or irradiance of the detector to the temperature. The rate of change in temperature depends on the laser absorption and scattering in the tissue. The temperature rise, ΔT, in the tissue can be calculated as $$\Delta T = \mu_a F t \frac{1}{\rho C_p}$$

with $\mu_a$ being the absorption coefficient of the tissue, F being the fluence rate, t being continuous lasing time on the tissue, ρ being the density of the tissue, and $C_p$ being the specific heat of the tissue.

The term "black body" was first used by Gustav Kirchhoff in 1860. In essence, all matter absorbs electromagnetic radiation to some degree and an object that absorbs all radiation falling on it (at all wavelengths and frequencies) is called a black body, i.e., a perfect absorber. When a black body is at a uniform temperature state, it emits back this absorbed energy, and it is termed as "black body radiation." This is a type of radiation and has continuous frequency and intensity which depends only on the black body's temperature, and the type of spectrum it generates is called the Planck spectrum. In this type of spectrum, spectral peaks at characteristic frequencies are shifted to higher values (shorter wavelengths) with increasing temperature values. For instance, at room temperature most of the emission of the black body is in the infrared region of the electromagnetic spectrum. At a typical environmental background temperature, which is around 300 K, the peak emission is at about 9.7 μm (and the curve covers the far infrared region as well). At around 1800 K (temperature of molten steel), the peak is shifted to 1.6 μm. At around 6000 K (surface temperature of the sun), the peak is shifting even further, 0.48 μm, which now is in the visible (blue) region of the spectrum. This type of shift in the emission peaks of the black bodies (to shorter wavelengths at higher temperatures) is governed by Wien's displacement law.

In living systems, in addition to the water molecules association with the electromagnetic field and effects of that, one has to consider the "meso-structure" effect where proteins and charged groups (located at specific sites on the proteins) are crucial for the overall biological activity. These specifically located charged groups associate with the water molecules and by doing this influence the dielectric behavior of the whole molecular-assembly, which in turn effects its biologic functioning. Thus, the dielectric properties of tissues (even at cellular level) depend on and vary with the water content.

In some embodiments, the temperature data measured by the temperature sensing assembly can be provided to a controller 1040, which can control the surgical laser 1010 to minimize thermal damage to the tissue. For example, low tissue temperature data, e.g., temperature much less than the critical temperature that the tissue can accept in order to prevent irreversible damages, can be used to increase the power of the surgical laser for a faster surgery process. High tissue temperature data, e.g., temperature reaching or approaching the critical temperature, can be used to decrease or not increase the power of the surgical laser to prevent irreversible damages to the tissue. Further, the rate of change of temperature can be used to regulate the laser power. For example, at zero rate of change, the temperature reaches steady state with the current power, and the surgery can proceed without temperature changes. A tissue temperature at a little below the critical temperature together with a zero rate of change can be an optimized tissue condition, e.g., a fastest surgical process without tissue damages. A low rate of change can allow a fast rate of change of the laser power without exceeding the critical temperature.

In some embodiments, other sensors can be included, such as a fluorescent meter or spectrometer, a near IR detector or spectrometer and a Raman spectrometer. The additional sensors can assist the surgeon in the surgery process, such as determining tissue characteristics to determine the critical temperature of reversible damages, and identifying tissues to determine whether the tissue is a healthy tissue or a cancerous tissue.

In some embodiments, a fluorescent sensing assembly 1030, which can include a fluorescent meter or spectrometer, can be included. The fluorescent sensing assembly can be coupled to the optical path from the optical fiber to receive input from the tissue, and coupled to the controller 1040 to provide fluorescent data stream to the controller. The fluorescent sensing assembly can detect fluorescent signal from the tissue. The fluorescent signal can be provided to the controller to determine tissue information, such as tissue characteristics and identification. The tissue information can complement the temperature sensing assembly 1070, such as to determine the critical reversible temperature of the tissue based on the tissue information.

In some embodiments, the surgical laser assembly 1000 can include different sensing assemblies, such as a fluorescent sensing assembly, a temperature sensing assembly, a Raman detecting assembly, a near IR signal sensing assembly, mini spectrometer, spectral camera and others. For example, the surgical laser assembly can include a Hamamatsu mini spectrometer such as spectrometer C13555MA using CMOS technology and covering from 340 nm to 830 nm with decent resolution, e.g., 2.3 nm FWHM. The surgical laser assembly can include an Avantes Miniature Spectroscopy, such as spectrometer AvaSpec-Mini 4096CL. Other sensors can be included, such as Si or InGaAs detector from Hammatsu with an optical line filter to observe specific wavelength and/or temperature of the tissue, or silicon photo diode such as S5821 or G12181, G12182, and G12183.

The multiple sensing assemblies can serve as a diagnostic tool for the surgery laser system, regarding tissue pathology, stone composition, cancerous or precancerous tissue precaution and warning. With detailed information of the tissue, a surgeon can select the right laser power, and laser pulse setting or mode to have a minimal invasive surgical procedure to deliver a high efficacy and safety surgery treatment, including reducing surgery time and hospital stay. The surgery laser system can also be integrated or incorporated to a robotic system, which can perform the surgical procedures automatically, semi-automatically, or under the control of a surgeon.

In some embodiments, the surgical laser operating conditions, including the duration of the laser pulses, the peak power of the laser, and the duty cycle of the laser, can be controlled to minimize hyperthermal effect.

In some embodiments, an infrared detection system can be used to determine the temperature of the tissue, for example, based on the black body radiation. In essence, all matter absorbs electromagnetic radiation to some degree and an object that absorbs all radiation falling on it (at all wavelengths and frequencies) is called a black body, e.g., a perfect absorber. When a black body is at a uniform temperature state, it emits back this absorbed energy, and it is termed as "black body radiation". This is a type of radiation and has a continuous frequency and intensity which depends only on the black body's temperature. The type of spectrum it generates is called the Planck spectrum. In this type of spectrum, spectral peaks at characteristic frequencies are shifted to higher values (shorter wavelengths) with increasing temperature values. For instance, at room temperature most of the emission of the black body is in the infrared region of the electromagnetic spectrum. At a typical environmental background temperature, which is around 300 K, the peak emission is at about 9.7 µm (and the curve covers the far infrared region as well). At around 1800 K (temperature of molten steel), the peak is shifted to 1.6 µm. At around 6000 K (surface temperature of the sun), the peak is shifting even further, 0.48 µm, which now is in the visible (blue) region of the spectrum. This type of shift in the emission peaks of the black bodies (to shorter wavelengths at higher temperatures) is governed by Wien's displacement law.

Figure 11A:
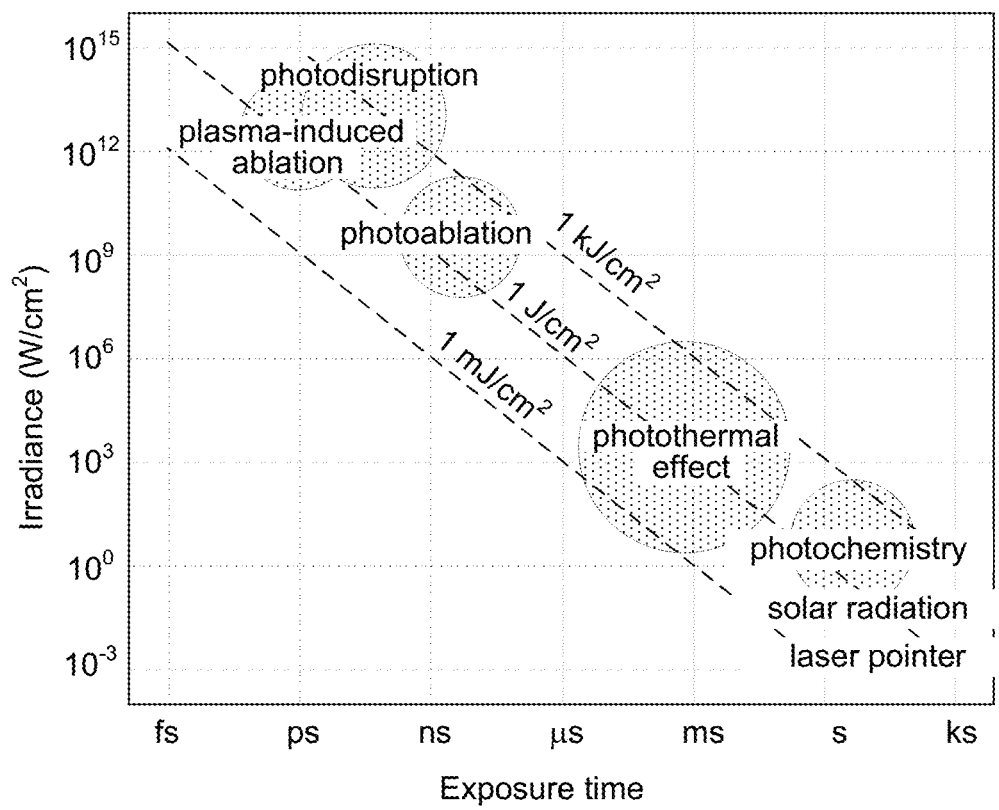
FIGS. 11A-11B illustrate characteristics of tissue-laser interactions according to some embodiments.
Figure 11B:
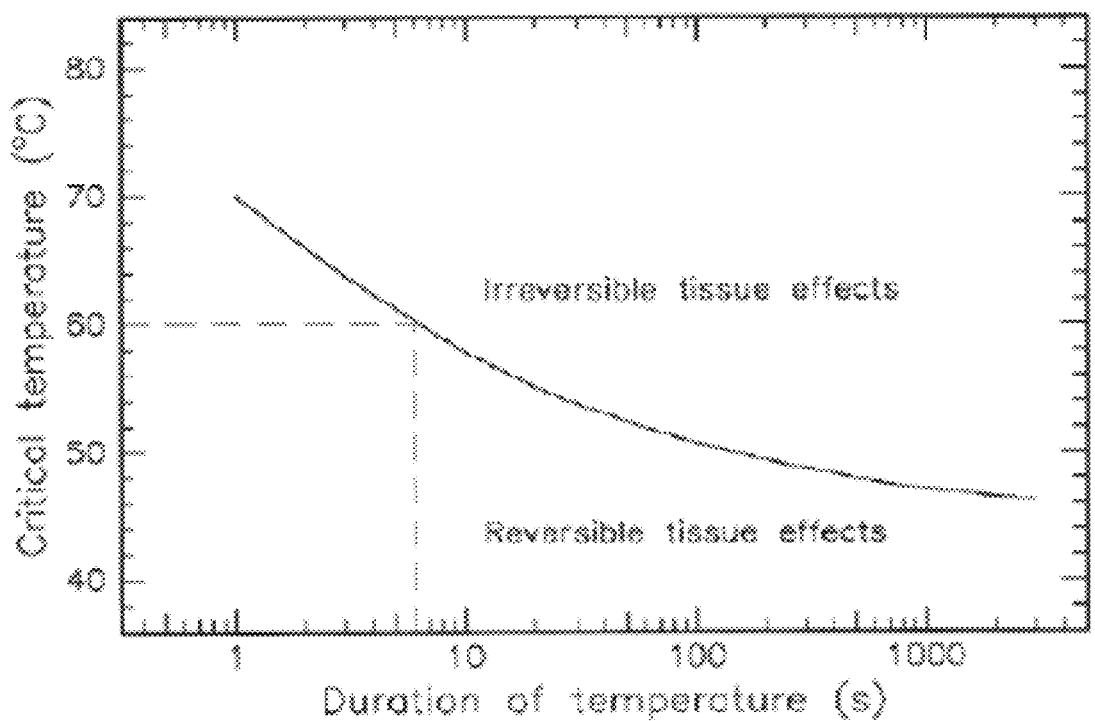

FIGS. 11A-11B illustrate characteristics of tissue-laser interactions according to some embodiments. FIG. 11A shows different laser-tissue interactions depend on the pulse duration of the light exposure and the irradiance, i.e., light energy delivered per unit area per unit time in $W/cm^2$. A surgical laser can operate in the microsecond to millisecond range, thus can operate in the photothermal area. At 120 Watts peak power pulse, the power density via 600 µm fiber delivery can be about 10 $kW/cm^2$. At 3 J per pulse of the laser, the power density via 600 µm fiber can reach 800 $kW/cm^2$. The laser pulse width can be determined to prevent hyperthermal effect, e.g., the tissue temperature rises too high, such as more than 60° C.

When the light absorption gives rise to an electronic transition, the more energetic electron will, on average, orbit the nuclei at a greater distance. As the attractive nuclear force falls off rapidly with distance, the electron will be less tightly bound, and will be able to form a chemical bond with another molecule more readily. This is the basis of photochemistry. While an excited molecule is undergoing intramolecular redistribution it might collide with another molecule. Some of the vibrational energy in the excited molecule will transferred to the colliding molecule as translational kinetic energy. Molecular translational kinetic energy is what appears at a macroscopic level as a temperature rise so leads to photothermal effects. This process of collisional relaxation will thereby thermalize the absorbed photon energy in a matter of picoseconds, although the resulting macroscopic thermal effects occur over very much longer timescales (milliseconds to seconds range).

When a molecule absorbs a photon of sufficient energy, the energy can be transferred to one of the molecule's electrons. An electron with higher energy can more easily escape the nuclear forces keeping it close to the nucleus, and so the excited molecules (which are molecules with an electron in a higher energy state) are more likely to undergo chemical reactions (exchanging or sharing of electrons) with other molecules. In photodynamic therapy, for instance, a photosensitizing drug (a concoction of molecules which, when they absorb light, cause reactive oxygen species to form) is used to cause necrosis (cell death) and apoptosis ('programmed' cell death). Photodynamic therapy is increasingly widely used in oncology to destroy cancerous tumors.

In some embodiments, the surgical laser can employ the photothermal interaction principle in which the energy of the photons absorbed by chromophores (a term used to refer to any light-absorbing molecules) is converted into heat energy via molecular vibrations and collisions, which can cause a range of thermal effects from tissue coagulation to vaporization. The photothermal interaction can be used for tissue cutting and welding in laser surgery.

FIG. 11B shows critical temperatures of a tissue as a function of the time that the tissue is at the temperature. The critical temperatures can form a boundary curve to separate the reversible effects and the irreversible effects. For example, a critical temperature of 60° C. is based on a duration of 6 seconds in which the tissue is at the 60° C.

In some embodiments, the surgical laser system can incorporate temperature and tissue sensors to optimize laser delivery settings for target the desired tissues and reduce surgical procedure times. For example, the critical temperature of a tissue can be calculated based on the expected duration of the exposure time. The calculated critical temperature then can be used as a temperature limit in the thermal tracking of the tissue temperature, e.g., to control the laser operating conditions so that the tissue temperature does not exceed the critical temperature, together with achieving the shortest surgical procedure time.

In some embodiments, the surgical laser is configured with laser pulse widths less than the thermal relaxation time of the target tissue to minimize thermal injury, based on the basic photothermolysis theory. The heat conduction time can be determined based on Furzikov studies $\tau=\delta^2/4\alpha$, in which $\delta$ is optical penetration depth of the incident radiation and $\alpha$ is thermal diffusivity.

In some embodiments, the surgical laser can be a laser in pulse mode, having wavelengths in the range between 1470 nm and 2100 nm, such as a 1470 nm laser, which can breakdown lipid structures by liquefying the lipids and breakdown tissue permanently. The surgical laser system can utilize the temperature sensing assembly to control the heat transfer to avoid heat spreading deeper into the tissue. For example, the laser pulse width can be at less than 1 millisecond. The detected thermal signal can be a combination of tissue heating and optical fiber heating, which can have different decay times due to the different thermal masses heat capacities. For example, the heated tissue can have a rapid decay while the optical fiber tip can have a longer decay. This difference can be used to separate the tissue thermal signal from other components. FIG. 12A-12C illustrate flow charts for operating a surgical laser system having a thermal tracking capability according to some embodiments. The surgical laser system can monitor the temperature of the tissue to control the surgical laser in order to prevent hyperthermal damages to the tissue.

In FIG. 12A, operation 1200 sets an operating condition of a surgical laser system based on a tissue temperature or a rate in the tissue temperature. The operating condition can include the power, the pulse width, and/or the intensity of the surgical laser. The operating condition can be determined so that the tissue temperature is less than a critical temperature at which the tissue undergoes irreversible damages. For example, a controller can control the surgical laser so that the instantaneous tissue temperature is less than the critical value. The critical temperature can be a function of the duration of the tissue temperature, which can be determined by an identification of the tissue characteristics. The controller can use the rate of change of the tissue temperature to regulate the surgical laser to prevent fast rise of the tissue temperature that can exceed the critical temperature. The controller can set a pulse width of the surgical laser to be less than the thermal relaxation or heat conduction of the tissue.

In FIG. 12B, operation 1220 obtains a tissue temperature or a rate of change of the tissue temperature under an operation of a surgical laser system. Operation 1230 changes an operating condition of the surgical laser system to obtain a steady tissue temperature during the operation.

In FIG. 12C, operation 1250 obtains a tissue temperature or a rate of change of the tissue temperature under an operation of a surgical laser system. Operation 1260 changes an operating condition of the surgical laser system to prevent irreversible tissue damage caused by the operation.

In some embodiments, a surgical laser system can incorporate a spectrometer for measuring spectral data, such as hyperspectral or multispectral signals from the tissue. The spectral data can provide additional information on the tissue, which can assist the surgeon or the robotic device in controlling the surgical laser during the surgery operation.

Figure 13:
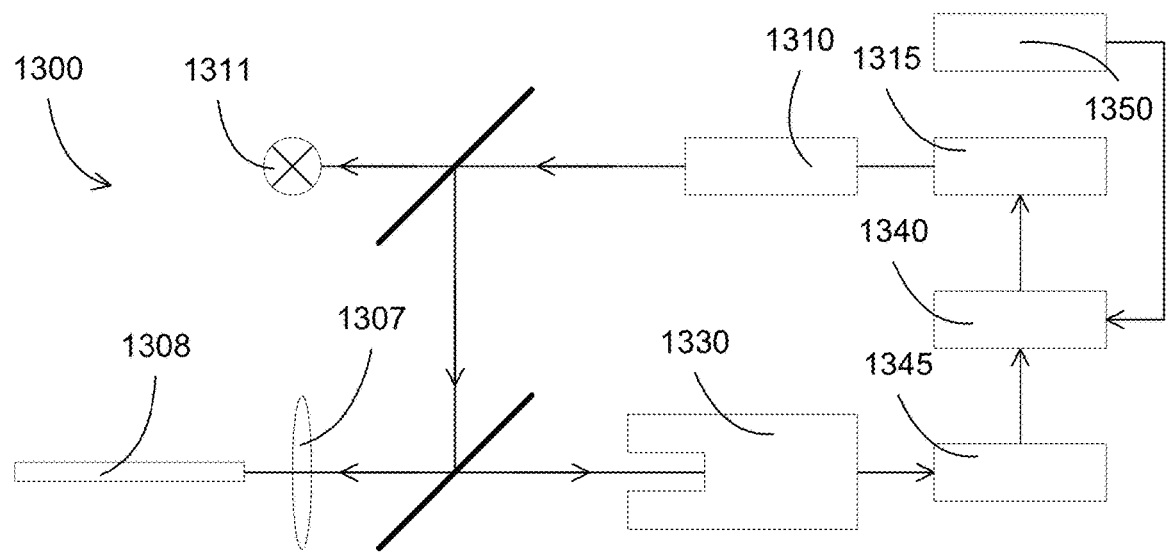
FIG. 13 illustrates a configuration of a surgical laser assembly without an external robotic interface according to some embodiments.

FIG. 13 illustrates a configuration of a surgical laser assembly without an external robotic interface according to some embodiments. The surgical laser system 1300 can include a surgical laser 1310, which can be a laser having wavelengths appropriate to the surgical operation, such as 1470-2100 nm. For example, the surgical laser can be configured for water and lipid absorption using wavelength of 1470 nm.

The surgical laser system 1300 can include an optical assembly, including a lens 1307, to bring the output of the surgical laser 1310 to an optical fiber 1308, the distal end of which can be inserted inside a patient for surgical operations. The optical assembly can include one or more beam splitter and mirror, which can direct the output of the surgical laser to the optical fiber 1308. An internal energy sensor 1311 can be included for measuring the output power of the surgical laser.

The surgical laser system 1300 can further include a spectrometer 1330, which can detect spectral data, e.g., signals at different wavelengths. The optical assembly can include a path for the spectral signal from the tissue to travel through the optical fiber 1308 to reach the spectrometer 1330.

Data collected from the spectrometer 1330 can be provided to a signal processing module 1345 before reaching a microprocessor 1340. The microprocessor 1340 can also receive inputs from the surgeon, such as from a touch screen user interface 1350. The microprocessor can control the power supply 1315 of the surgical laser 1310, which can vary the duty cycle, pulse width and/or pulse rate of the surgical laser. The microprocessor can process temperature data plus the tracking position of tissue target, and can send a data stream to assist robotic device in surgery. Other components can be included, such as an internal energy sensor for measuring the output power of the surgical laser, a control system for controlling the aiming lasers, aiming lasers with different wavelengths, an infrared tissue temperature sensor for monitoring the temperature of the tissue, and a fiber protection sensor for protecting the optical fiber.

In some embodiments, a surgical laser system can incorporate a temperature sensing assembly, such as an infrared temperature sensor for measuring the tissue temperature as determined by a black body radiation. The tissue can emit radiant energy, e.g., thermal radiation, which can be a result of the temperature of the tissue. Also, the rate of change of the temperature can depend on the laser absorption and scattering in the tissue. The temperature data can provide information regarding the status of the tissue, such as how much longer the tissue can be exposed to the laser without being damages. The tissue temperature can serve as an end-point for the laser surgical procedures, together with improving safety and efficacy by preventing the tissue from reaching a damage temperature, such as from hyperthermia. Hyperthermia is a reaction of heat transfer to the tissue below 60° C. It could be collagen gelatinization and subsequently coagulation of the tissue, or the denaturation of cell membranes or cytoplasmic proteins leading to necrotic or apoptotic cell death. Coagulative necrosis is a type of accidental cell death typically caused by ischemia or infarction. It is characterized by the 'ghostly' appearance of cells under light microscopy in the affected area of tissue.

The temperature sensing assembly can detect the IR flux from the tissue, for example, during the off time of the laser pulse stream. The temperature sensing assembly or a microcontroller can also detect or determine the rate of change of temperature on the tissue after each laser pulse.

The rate of change of temperature has a temporal relationship to the laser pulse. The rate of change in temperature can be different with endoscopic light.

The IR detector can be a pyrometer with sensitive to wavelength from 1.7 to 2.2 um, such as visible light Si (silicon) detector or extended InGaAs detector, which can be sensitive in 1.7 um to 2.5 um range.

In some embodiments, a surgical laser can include visible light, such as laser diode or SLED light, which can serve as aiming beam and tracking. The visible light can include wavelength 532 nm±20 nm (green color), 635 nm±20 nm (red color), and 365-440 nm (blue color). The surgical laser can include infrared thermal tracking and visible light positioning. Thermal tracking could also be employed by an IR camera of a robotic device.

Figure 14A:
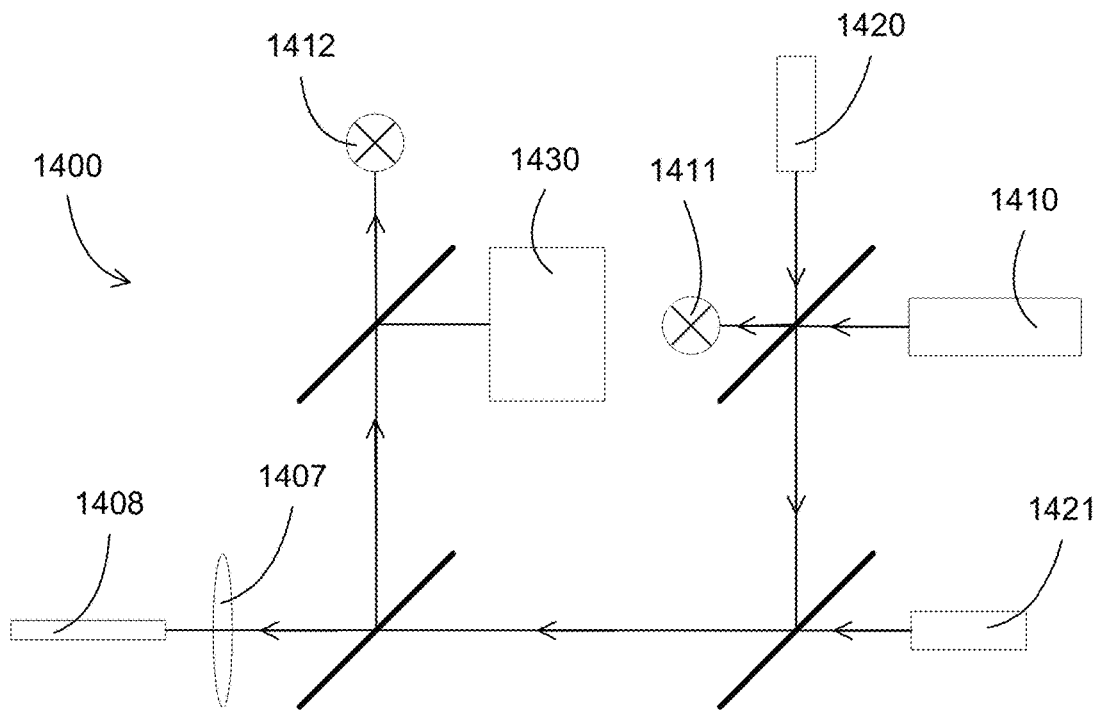
FIGS. 14A-14G illustrate configurations for surgical laser systems having infrared detecting assembly according to some embodiments.

FIGS. 14A-14G illustrate configurations for surgical laser systems having infrared detecting assembly according to some embodiments. In FIG. 14A, a surgical laser system 1400 can include a design sensor position for tissue monitoring. The surgical laser system 1400 can include a surgical laser 1410, which can be a laser having wavelengths appropriate to the surgical operation, such as 1470-2100 nm. For example, the surgical laser can be configured for water and lipid absorption using wavelength of 1470 nm.

The surgical laser system 1400 can include an optical assembly, including a lens 1407, to bring the output of the surgical laser 1410 to an optical fiber 1408, the distal end of which can be inserted inside a patient for surgical operations. The optical assembly can include one or more beam splitter and mirror, which can direct the output of the surgical laser to the optical fiber 1408. An internal energy sensor 1411 can be included for measuring the output power of the surgical laser.

The surgical laser system can include one or more aiming lasers, with a blue aiming laser 1420 (365-440 nm) and a green aiming laser 1421 (535±90 nm) shown, which can reach the optical assembly to merge with the surgical laser. Other aiming lasers with different wavelengths can be included, such as a red aiming laser.

The surgical laser system 1400 can further include an infrared tissue temperature sensor 1412, which can include an infrared detector, such as detecting short wavelength infrared between 1.7 and 2.2 micrometer, together with support circuitries. The optical assembly can include a path for the infrared signal from the tissue to travel through the optical fiber 1408 to reach the infrared tissue temperature sensor 1412.

The infrared detector can monitor the temperature of the tissue, for example, to prevent damage to the tissue by laser heating. The infrared detector can be an infrared sensor, an infrared imaging camera, or an infrared spectrometer for determining the spatial or spectral tissue temperature.

The surgical laser system 1400 can further include other tissue sensor assemblies 1430, such as a Raman sensor to assist in the identification of tissue (such as to monitor hard and soft tissue, and a near infrared camera for thermal tracking. The sensor assemblies can include a photomultiplier detector for amplifying the signal.

Other components can be included, such as a control system for controlling the aiming lasers, aiming lasers with different wavelengths, and a fiber protection sensor for protecting the optical fiber.

Figure 14B:
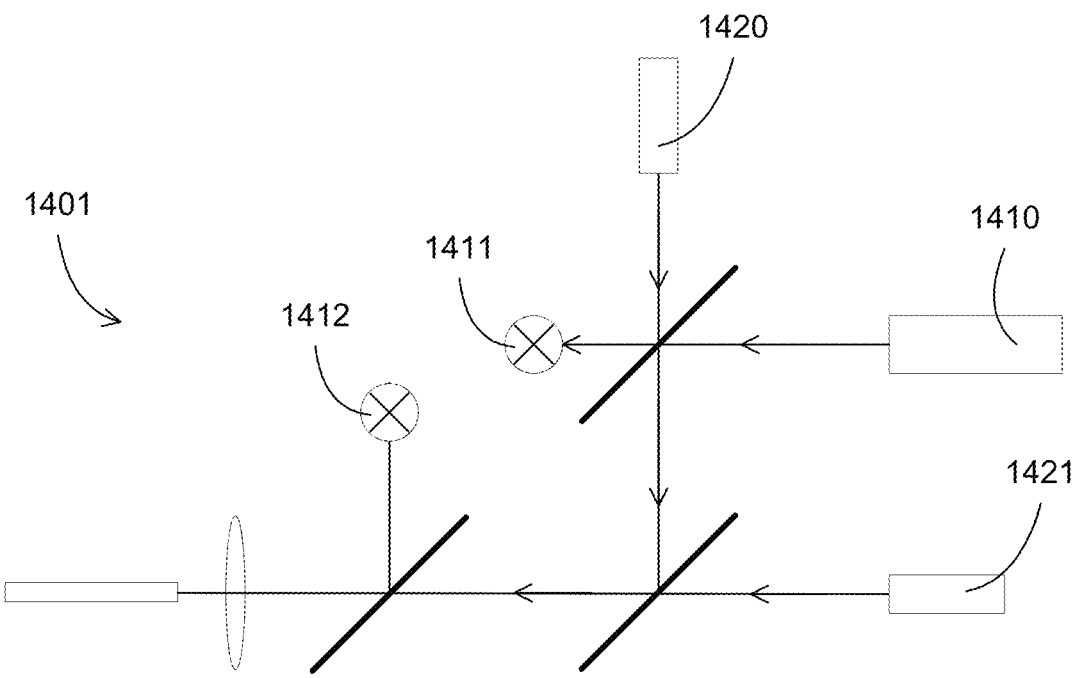

FIG. 14B shows a configuration for a surgical laser system 1401 having a single IR detector for tissue temperature. The surgical laser system can include a surgical laser 1410, which can be a laser having wavelengths appropriate to the surgical operation, such as 1470-2100 nm. For example, the surgical laser can be configured for water and lipid absorption using wavelength of 1470 nm.

The surgical laser system can include an optical assembly, including a lens and an optical fiber, together with beam splitter and mirror. An internal energy sensor 1411 can be included for measuring the output power of the surgical laser.

The surgical laser system can include one or more aiming lasers, with a blue aiming laser 1420 (365-440 nm) and a green aiming laser 1421 (535±90 nm) shown, which can reach the optical assembly to merge with the surgical laser. Other aiming lasers with different wavelengths can be included, such as a red aiming laser.

The surgical laser system can further include an infrared tissue temperature sensor 1412, which can include an infrared detector, such as detecting short wavelength infrared between 1.7 and 2.2 micrometer, together with support circuitries. The optical assembly can include a path for the infrared signal from the tissue to travel through the optical fiber to reach the infrared tissue temperature sensor 1412.

Other components can be included, such as a control system for controlling the aiming lasers, aiming lasers with different wavelengths, and a fiber protection sensor for protecting the optical fiber.

Figure 14C:
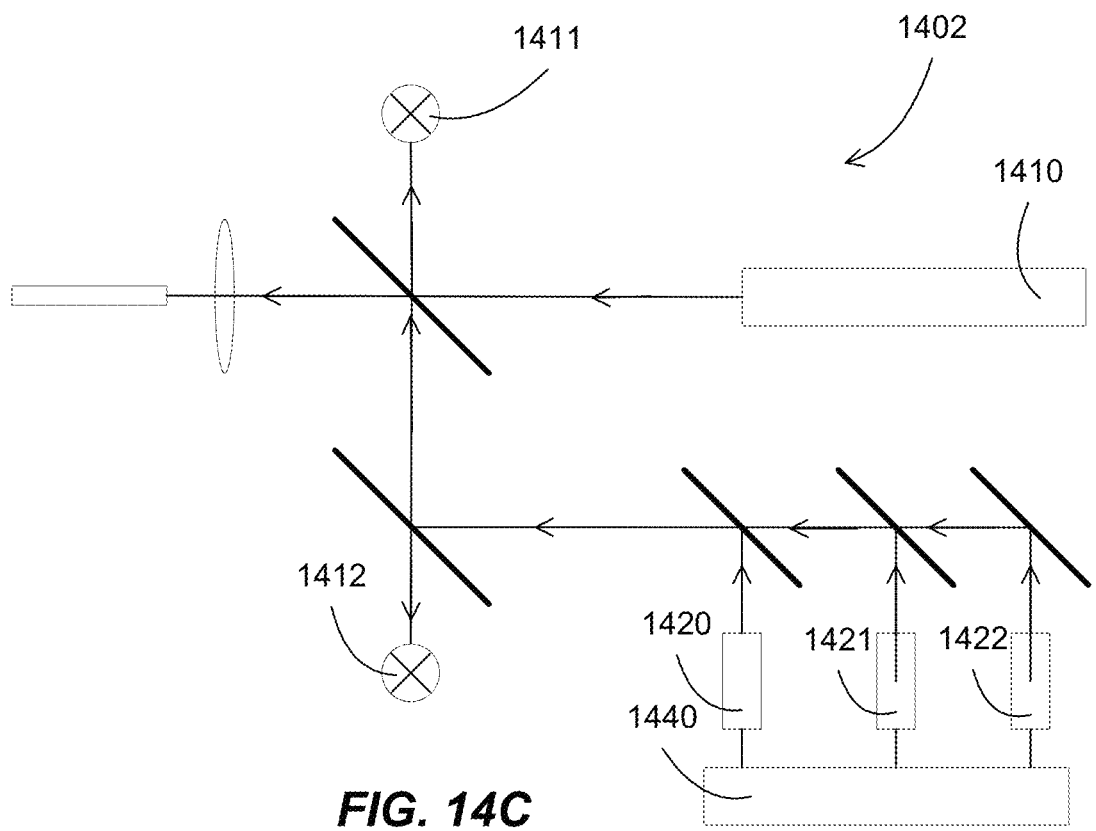

FIG. 14C shows a surgical laser system 1402 with a tissue temperature and 3-color aiming design. The surgical laser system can include a surgical laser 1410, which can be a laser having wavelengths appropriate to the surgical operation, such as 1470-2100 nm. For example, the surgical laser can be configured for water and lipid absorption using wavelength of 1470 nm. The surgical laser system can include an optical assembly, including a lens and an optical fiber, together with beam splitter and mirror. An internal energy sensor 1411 can be included for measuring the output power of the surgical laser.

The surgical laser system can include three aiming lasers, including a blue aiming laser 1420 (365-440 nm), a green aiming laser 1421 (535±90 nm), and a red aiming laser 1422 (635±20 nm). The aiming lasers can be controlled by a microprocessor 1440, such as selecting the aiming lasers to provide to the optical fiber, e.g., The surgical laser system can further include an infrared tissue temperature sensor 1412, which can include an infrared detector, such as detecting short wavelength infrared between 1.7 and 2.2 micrometer, together with support circuitries. The optical assembly can include a path for the infrared signal from the tissue to travel through the optical fiber to reach the infrared tissue temperature sensor 1412.

The infrared detector can monitor the temperature of the tissue, for example, to prevent damage to the tissue by laser heating. The infrared detector can be an infrared sensor, an infrared imaging camera, or an infrared spectrometer for determining the spatial or spectral tissue temperature. Other components can be included, such as a control system for controlling the aiming lasers, aiming lasers with different wavelengths, and a fiber protection sensor for protecting the optical fiber.

In some embodiments, the present invention discloses a robotic surgical device with a laser delivery system including temperature, imaging tracking, and/or fluorescent sensors. The robotic surgical device can control the laser delivery system with inputs from the sensing data of temperature, imaging tracking, and/or fluorescent sensors.

In some embodiments, the robotic surgical device can include a laser delivery system using an infrared sensor detection system for temperature and imaging tracking, together with other tissue sensing abilities such as Raman spectrometer and near infrared camera systems.

Figure 14D:
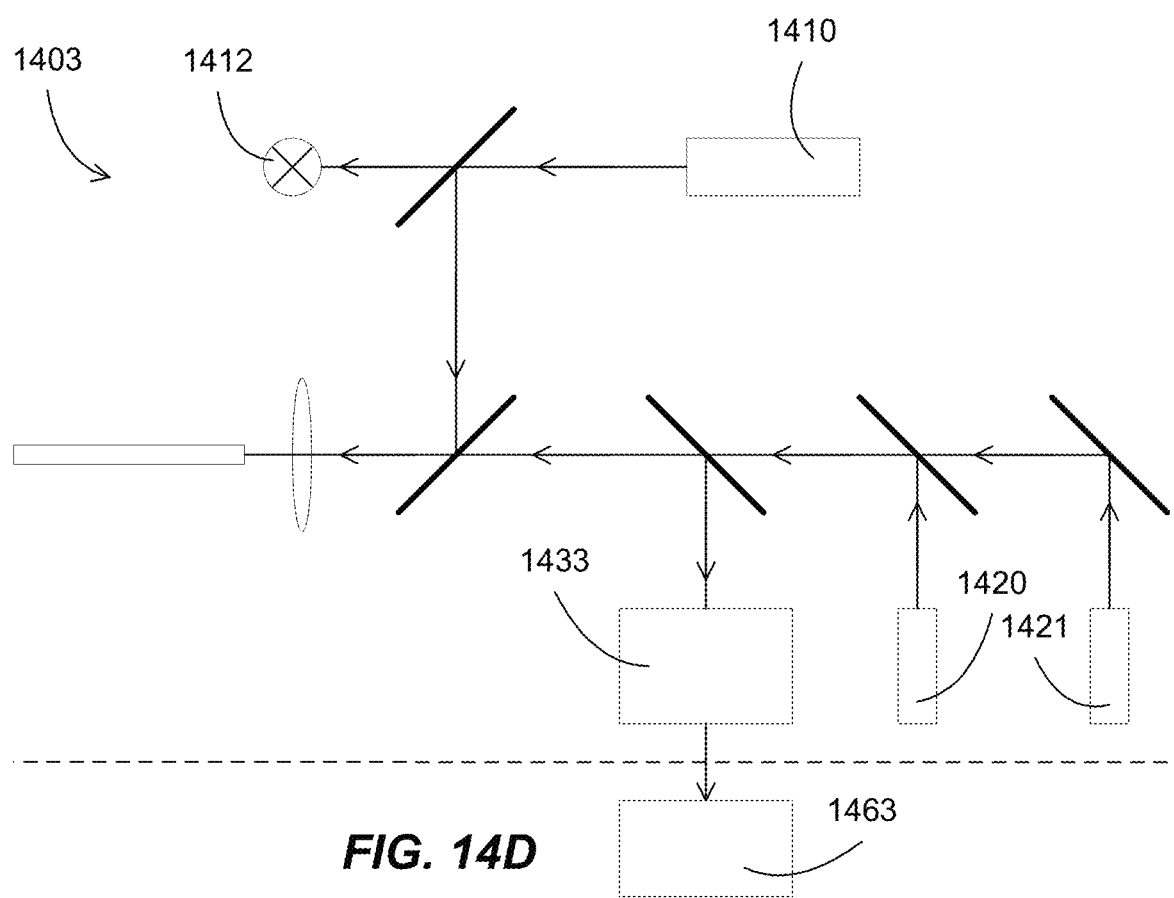

In FIG. 14D, a surgical laser system 1403 can include two aiming beams and multiple sensors to connect to an external robotic device or patient monitor system. The surgical laser system can include a surgical laser 1410, which can be a laser having wavelengths appropriate to the surgical operation, such as 1470-2100 nm. For example, the surgical laser can be configured for water and lipid absorption using wavelength of 1470 nm. The surgical laser system can include an optical assembly, including a lens and an optical fiber, together with beam splitter and mirror. The surgical laser system can include one or more aiming lasers, with a blue aiming laser 1420 (365-440 nm) and a green aiming laser 1421 (535±90 nm) shown, which can reach the optical assembly to merge with the surgical laser. Other aiming lasers with different wavelengths can be included, such as a red aiming laser.

The surgical laser system can further include an infrared tissue temperature sensor 1412, which can include an infrared detector, such as detecting short wavelength infrared between 1.7 and 2.2 micrometer, together with support circuitries. The optical assembly can include a path for the infrared signal from the tissue to travel through the optical fiber to reach the infrared tissue temperature sensor 1412.

The surgical laser system can further include a controller 1433, which can be used to process the data from the infrared tissue temperature sensor. The controller can also be configured to process data from other tissue sensor assemblies, such as a Raman sensor to assist in the identification of tissue (such as to monitor hard and soft tissue, and a near infrared camera for thermal tracking. The sensor assemblies can include a photomultiplier detector for amplifying the signal. The controller can communicate with an external robotic device or system 1463 for controlling the movements of the surgical laser system, including controlling the characteristics of the surgical laser and the aiming lasers, for example, based on inputs from a surgeon and/or from the processed data from the tissue sensor system, such as from the infrared detector, the Raman sensor, and the near infrared thermal tracking system.

Other components can be included, such as an internal energy sensor for measuring the output power of the surgical laser, a control system for controlling the aiming lasers, aiming lasers with different wavelengths, and a fiber protection sensor for protecting the optical fiber.

Figure 14E:
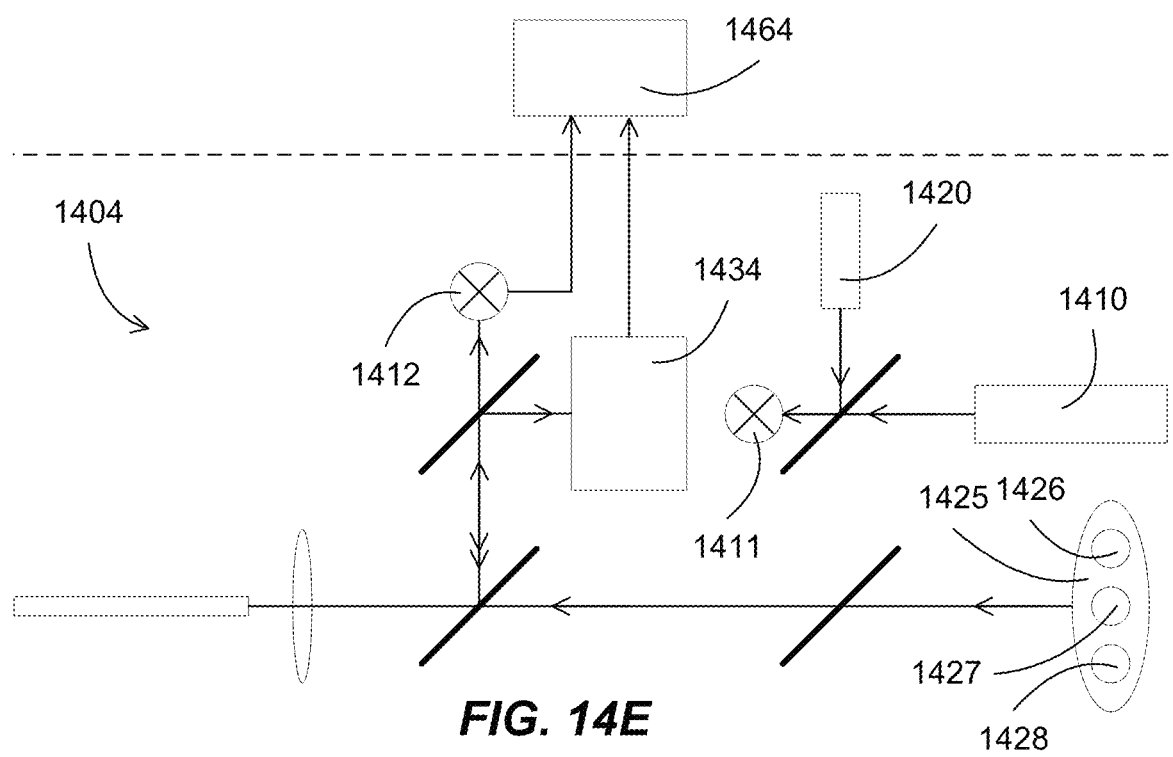

In FIG. 14E, a surgical laser system 1404 can include a 3-color aiming beam and external robotic device interface. The surgical laser system can monitor tissue temperature, tissue spectral and amplitude characteristics. The surgical laser system can include a surgical laser 1410, which can be a laser having wavelengths appropriate to the surgical operation, such as 1470-2100 nm. For example, the surgical laser can be configured for water and lipid absorption using wavelength of 1470 nm.

The surgical laser system can include an optical assembly, including a lens and an optical fiber, together with beam splitter and mirror. An internal energy sensor 1411 can be included for measuring the output power of the surgical laser.

The surgical laser system can include multiple aiming lasers, such as an aiming laser 1420, together with a rotating aiming laser system 1425, which, as shown, includes three aiming lasers 1426, 1427, and 1428 mounted on a rotating disc, which is controlled by a motor, such as a stepper motor for switching between different lasers. The aiming lasers can be different color low power (e.g., 1-100 mW power) laser diodes, such as blue, green and red. The rotating system can allow a selection of aiming lasers, e.g., one or more color lasers can be provided at one time.

The surgical laser system can further include an infrared tissue temperature sensor 1412, which can include an infrared detector, such as detecting short wavelength infrared between 1.7 and 2.2 micrometer, together with support circuitries. The optical assembly can include a path for the infrared signal from the tissue to travel through the optical fiber to reach the infrared tissue temperature sensor 1412.

The infrared detector can monitor the temperature of the tissue, for example, to prevent damage to the tissue by laser heating. The infrared detector can be an infrared sensor, an infrared imaging camera, or an infrared spectrometer for determining the spatial or spectral tissue temperature.

The surgical laser system can further include other tissue sensor assemblies 1434, such as a Raman sensor to assist in the identification of tissue (such as to monitor hard and soft tissue, and a near infrared camera for thermal tracking. The sensor assemblies can include a photomultiplier detector for amplifying the signal.

Data from the infrared tissue temperature sensor 1412 and other tissue sensor assemblies 1434 can be provided to an external robotic device or system 1464 for controlling the movements of the surgical laser system, including controlling the characteristics of the surgical laser and the aiming lasers, for example, based on inputs from a surgeon and/or from the processed data from the tissue sensor system, such as from the infrared detector, the Raman sensor, and the near infrared thermal tracking system.

Other components can be included, such as a control system for controlling the aiming lasers, aiming lasers with different wavelengths, and a fiber protection sensor for protecting the optical fiber.

Figure 14F:
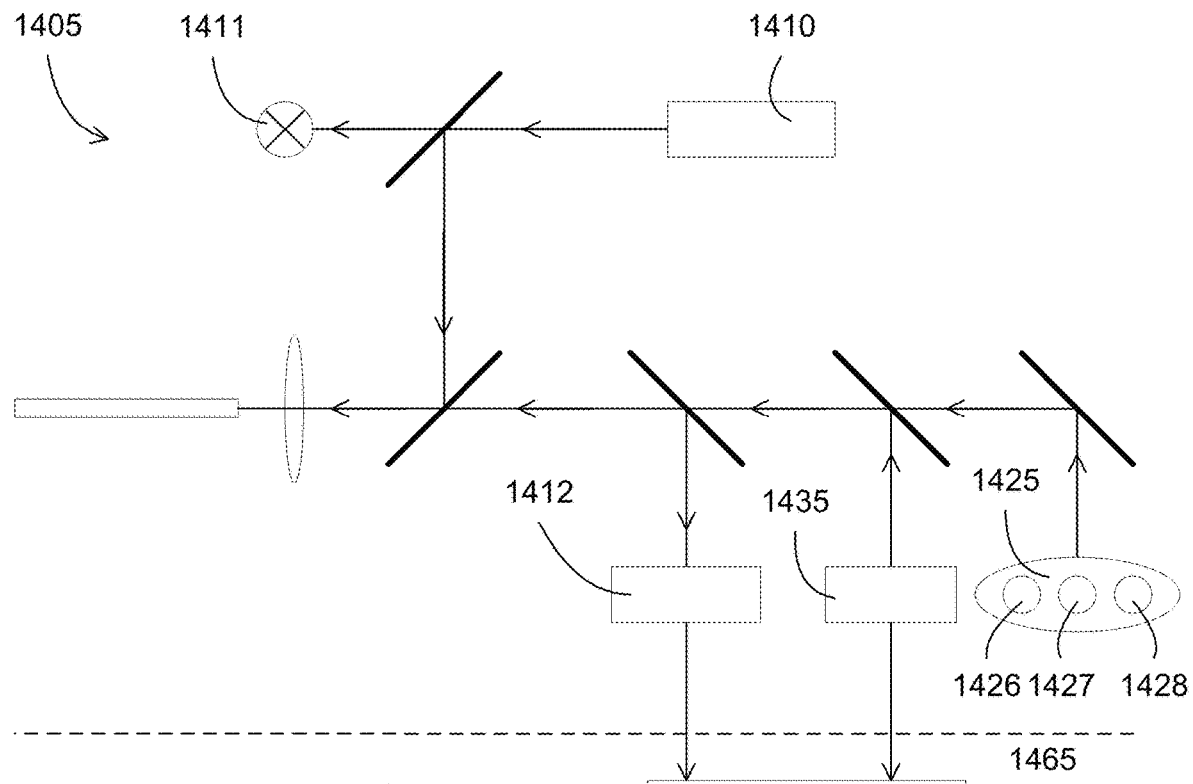

In FIG. 14F, a surgical laser system 1405 can include a 3-color aiming beam and external robotic device interface. The surgical laser system can include a surgical laser 1410, which can be a laser having wavelengths appropriate to the surgical operation, such as 1470-2100 nm. For example, the surgical laser can be configured for water and lipid absorption using wavelength of 1470 nm.

The surgical laser system can include an optical assembly, including a lens and an optical fiber, together with beam splitter and mirror. An internal energy sensor 1411 can be included for measuring the output power of the surgical laser.

The surgical laser system can include a rotating aiming laser system 1425, which, as shown, includes three aiming lasers 1426, 1427, and 1428 mounted on a rotating disc, which is controlled by a motor, such as a stepper motor for switching between different lasers. The aiming lasers can be different color low power (e.g., 1-5 mW power) laser diodes, such as blue, green and red. The rotating system can allow a selection of aiming lasers, e.g., one or more color lasers can be provided at one time.

The surgical laser system can further include an infrared tissue temperature sensor 1412, which can include an infrared detector, such as detecting short wavelength infrared between 1.7 and 2.2 micrometer, together with support circuitries. The optical assembly can include a path for the infrared signal from the tissue to travel through the optical fiber to reach the infrared tissue temperature sensor 1412.

The surgical laser system can further include other tissue sensor assemblies 1435, such as a Raman sensor to assist in the identification of tissue (such as to monitor hard and soft tissue, and a near infrared camera for thermal tracking. The sensor assemblies can include a photomultiplier detector for amplifying the signal.

The infrared detector and the other tissue sensor assemblies can monitor the characteristics the tissue, for example, to determine proper conditions for the surgical laser and the aiming lasers. Data from the infrared tissue temperature sensor and other tissue sensor assemblies can be provided to an external robotic device or system 1465 for controlling the movements of the surgical laser system, including controlling the characteristics of the surgical laser and the aiming lasers, for example, based on inputs from a surgeon and/or from the processed data from the tissue sensor system, such as from the infrared detector, the Raman sensor, and the near infrared thermal tracking system.

Other components can be included, such as a control system for controlling the aiming lasers, aiming lasers with different wavelengths, and a fiber protection sensor for protecting the optical fiber.

Figure 14G:
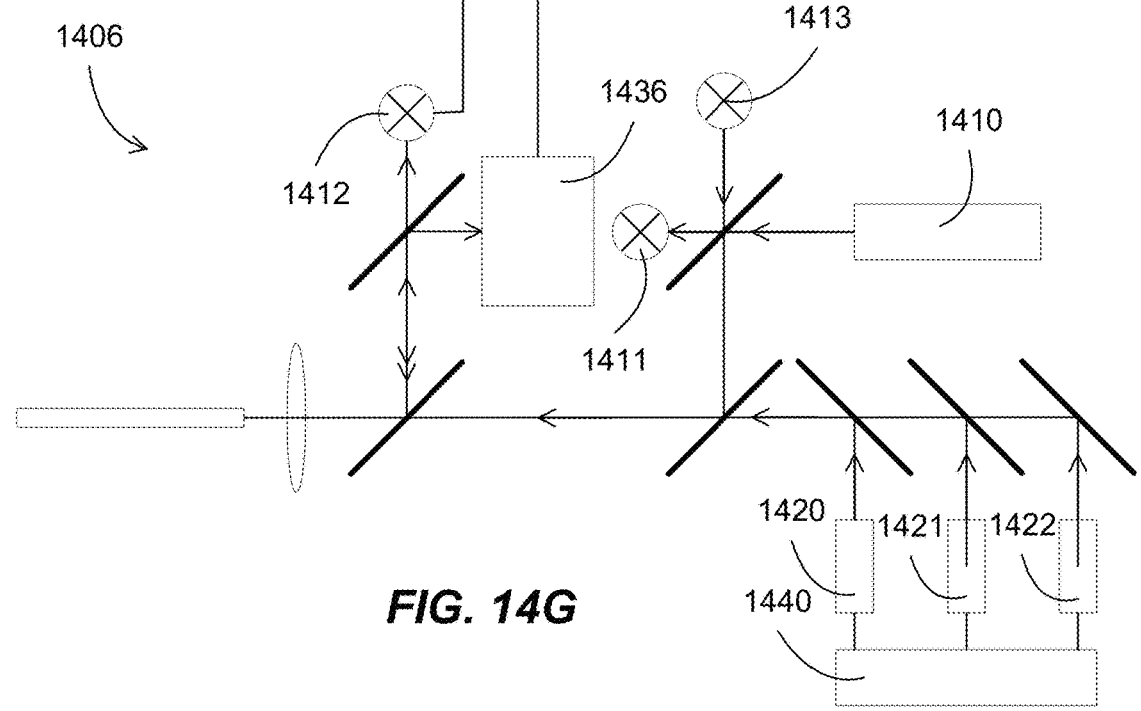

In FIG. 14G, a surgical laser system 1406 can include a 3-color aiming beam and external robotic device interface. The surgical laser system can include a surgical laser 1416, which can be a laser having wavelengths appropriate to the surgical operation, such as 1470-2100 nm. For example, the surgical laser can be configured for water and lipid absorption using wavelength of 1470 nm or breaking stones using a Holmium laser, e.g., a pulsed laser having 2100 nm wavelength.

The surgical laser system can include an optical assembly, including a lens and an optical fiber, together with beam splitter and mirror. An internal energy sensor 1411 can be included for measuring the output power of the surgical laser.

The surgical laser system can include an optical distribution of multiple aiming laser system, which, as shown, includes three aiming lasers 1420, 1421, and 1422 controlled by a microprocessor control 1440 for selecting aiming lasers, e.g., one or more aiming lasers can be provided at one time. The aiming lasers can be different color low power (e.g., 1-5 mW power) laser diodes, such as blue, green and red.

The surgical laser system can further include an infrared tissue temperature sensor 1412, which can include an infrared detector, such as detecting short wavelength infrared between 1.7 and 2.2 micrometer, together with support circuitries. The optical assembly can include a path for the infrared signal from the tissue to travel through the optical fiber to reach the infrared tissue temperature sensor 1412.

The surgical laser system can further include other tissue sensor assemblies 1436, such as a Raman sensor to assist in the identification of tissue (such as to monitor hard and soft tissue, and a near infrared camera for thermal tracking. The sensor assemblies can include a photomultiplier detector for amplifying the signal.

The infrared detector and the other tissue sensor assemblies can monitor the characteristics the tissue, for example, to determine proper conditions for the surgical laser and the aiming lasers. Data from the infrared tissue temperature sensor and other tissue sensor assemblies can be provided to an external robotic device or system 1466 for controlling the movements of the surgical laser system, including controlling the characteristics of the surgical laser and the aiming lasers, for example, based on inputs from a surgeon and/or from the processed data from the tissue sensor system, such as from the infrared detector, the Raman sensor, and the near infrared thermal tracking system.

Other components can be included, such as a control system for controlling the aiming lasers, aiming lasers with different wavelengths, and a fiber protection sensor for protecting the optical fiber.

In some embodiments, the robotic surgical device can include a laser delivery system using an infrared sensor detection system for temperature and imaging tracking, together with other tissue sensing abilities such as Raman spectrometer, near infrared camera systems, and fluorescent detection system. The fluorescent detection system can use aiming lasers of the laser delivery system as excitation sources for the tissue underwent surgery.

In some embodiments, the present invention discloses a surgical laser system, and methods forming and operating the surgical laser system, that can be configured to collect an adequate amount of data to assist in the optimization of setting and operation parameters of the surgical laser. To have sufficient data to analyze the tissue under the surgery, the data collection might need to be as long as possible. And since the surgical laser beam can present a strong background noise, the data can be collected during the off time of the laser pulse, e.g., when there is no laser beam reaching the tissue.

In some embodiments, the surgical laser system can operate the laser for image collection with high-speed, real-time, two- and three-dimensional imaging processes, using the off time of the laser pulses for data collection. The capability of real-time high-speed optical imaging can be essential for capturing the evolution of dynamic events of the tissue undergoing the surgery. For example, achieving reliable real-time, high-speed optical microscopy can provide the key to tissue identification using dynamical behaviors of different tissue types.

Timely acquisition of the tissue data can be critical during a surgery operation. A timely data acquisition can allow identification of surrounding tissues for the navigation and the treatment using the laser. A fast data acquisition process thus can provide complete tissue information before the laser action, which can be achieved by high speed data acquisition electronics. In addition, data collected during the off time of the laser can provide a high signal to noise ratio. In some embodiments, the data acquisition modules of the surgical laser system can use image microscopy with high sensitivity for both time and frequency domains for tissue inspection during laser surgery processes. A long data acquisition time is needed to collect all the necessary tissue information, which can be accomplished by a long off time of the laser pulses. Sampling of the tissue signal can take place while the laser source is switched off briefly, e.g. in the off time of the surgical laser pulses, so that the high intensity output beam of the surgical laser will not overwhelm the tissue signal from light returning through the optical fiber. The signal-to-noise ratio of the tissue signal can be improved by using a phase-locked loop to eliminate other signals that are not in phase with the off periods of the laser source.

In some embodiments, the present invention discloses a surgical laser system having the sensors performing data acquisition during the laser off time to avoid laser dominated signal and interference. In addition, the surgical laser system can have long off time to allow the multiple sensors to detect, monitor, and achieve multiple data acquisition cycles to verify and validate results. The long off time can be achieved by reducing duty cycle while increasing the peak power of the surgical laser to maintain constant average power, e.g., the power of the surgical laser is changed by changing the duty cycle of the surgical laser, e.g., changing the laser pulse width while maintaining the laser period.

Figure 15A:
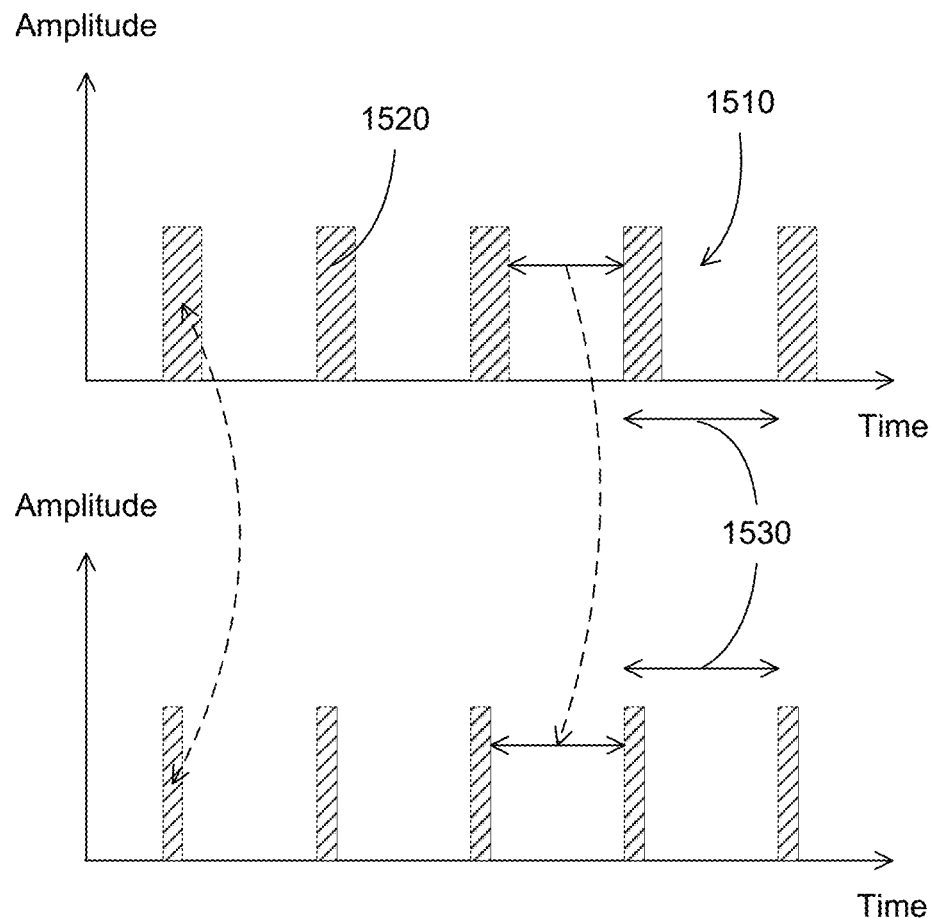
FIGS. 15A-15B illustrate variations of the pulses of the surgical laser according to some embodiments.
Figure 15B:
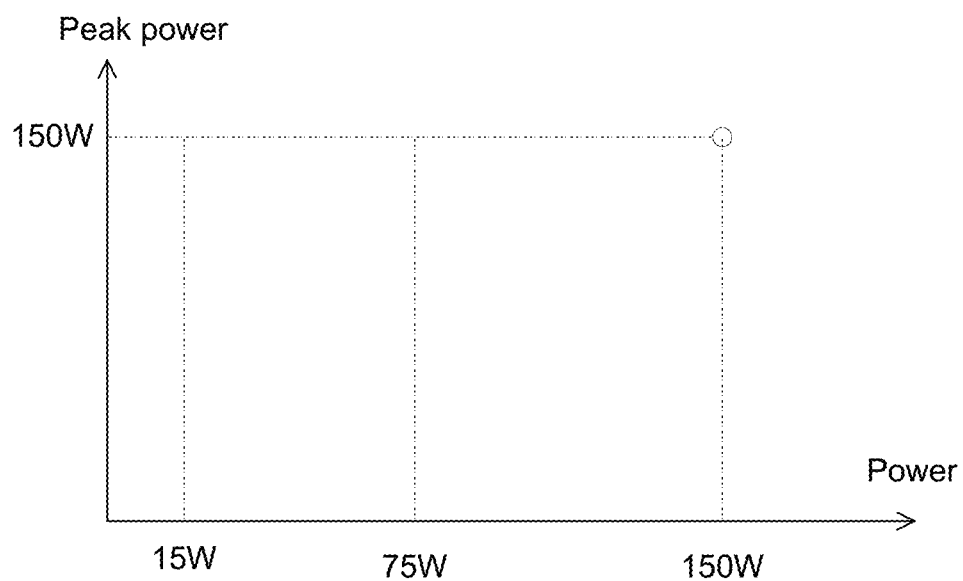

FIGS. 15A-15B illustrate variations of the pulses of the surgical laser according to some embodiments. A laser pulse stream can include pulses 1520 followed by an off time 1510. The power of the laser pulses can be determined by the areas of the pulses 1520. Thus the power of the laser can be changed by varying the pulse width while keeping the pulse period 1530 and the pulse amplitude constant. In FIG. 15A, the laser power can be reduced by 50% by a reduction in the on time of the laser pulses, which can provide a longer off time for data acquisition.

In some embodiments, the surgical laser can have the average power changed by changing the laser pulse width, while keeping the peak power of the laser constant. For example, if the peak power is 200 Watts, to achieve an average laser power of 100 W, the duty cycle can be set at 50%, e.g., for every millisecond, the laser is on for 0.5 ms and off for 0.5 ms. To achieve an average laser power of 20 W, the duty cycle can be set at 10%, e.g., for every millisecond, the laser is on for 0.1 ms and off for 0.9 ms. This configuration of varying laser duty cycle can provide a long off time for the data acquisition process.

In some embodiments, the duty cycles can vary from a minimum value to a maximum value. The minimum value can be set at a value to allow a precision of the laser average power. For example, the minimum value of the duty cycle can be greater than 1%, 2%, 5%, 10%, or 20% to ensure the precision of the laser power setting. The maximum value can be set at a value to allow adequate off time for the data acquisition process. For example, the maximum value of the duty cycle can be less than 75%, 50%, 40%, or 30% to ensure a long off time. Thus, the peak power of the laser can be at multiple times of maximum average power. For example, the maximum average power can be 100 W, but the peak power can be 150 W (for a maximum duty cycle of 67%), 200 W (for a maximum duty cycle of 50%), 300 W (for a maximum duty cycle of 33%), or 500 W (for a maximum duty cycle of 25%), In some embodiments, the minimum and maximum values of the duty cycle can be determined based on the surgical laser system configuration.

FIG. 15B shows an example curve of the peak power as a function of the average power of the surgical laser. The peak power can be set at 150 W power. The operation range of the laser power can be from a minimum of 15 W for a minimum of 10% duty cycle, to a maximum of 75 W for a maximum of 50% duty cycle. Lower operation power of the laser can be achieved by reducing the peak power, such as lower to 100 W of peak power. Higher operation power of the laser can be achieved by increasing the peak power, such as increasing to 300 W of peak power. In some embodiments, the laser pulse period can be constant, such as at 1 millisecond.

In some embodiments, the present invention discloses methods for operating a surgical laser system for optimum surgical procedures, such as with high precision and shorter surgery time. The optimum surgical procedures can be accomplished through an extensive data acquisition process to allow an accurate determination of the surgery critical parameters, such as the tissue characteristics for a proper determination of the laser operating conditions. The extensive data acquisition process can be accomplished by providing long off time of the laser pulses, e.g., small duty cycle of the laser pulses.

In some embodiments, the power of the surgical laser can be varied by changing the duty cycle. For example, a peak power of the laser can be determined. Then the laser power can be varied from a minimum power value to a maximum power value by varying the duty cycle. Different peak power settings can be used to allow a minimum off time, which can be determined by the data acquisition process.

In some embodiments, the peak power and the power of the surgical laser can be determined by a thermal capability of the tissue. For example, hyperthermal damages can be formed at temperature above 60 C for a typical tissue. By determining the tissue characteristics using different sensing assemblies, such as fluorescent sensing assembly, Raman spectrometer, and near IR spectrometer, the irreversible temperature of the tissue undergone the surgery process can be determined, which can lead to a determination of the peak power of the laser without tissue damages. In addition, the tissue characteristics can be used to determine the laser operating conditions, which can be used to calculate the surgical time. The surgical time can also be used in the determination of the critical temperature of irreversible damages, since the critical temperature can be lower for longer surgical times.

Figure 16A:
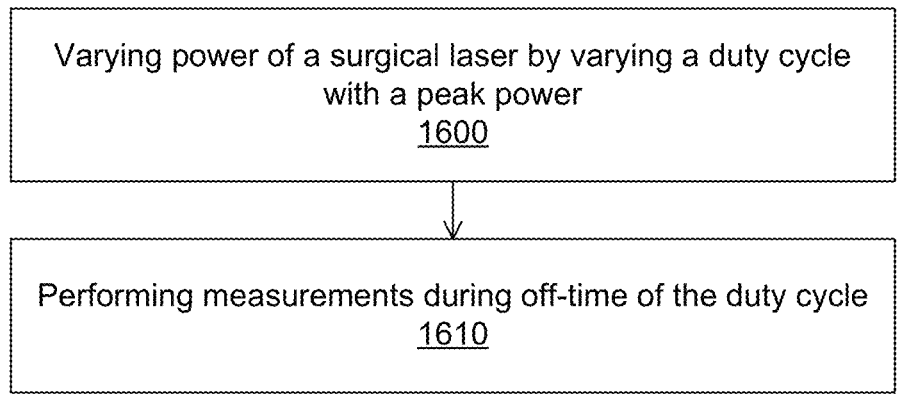
FIGS. 16A-16B illustrate flow charts for optimizing a surgery laser system according to some embodiments.
Figure 16B:
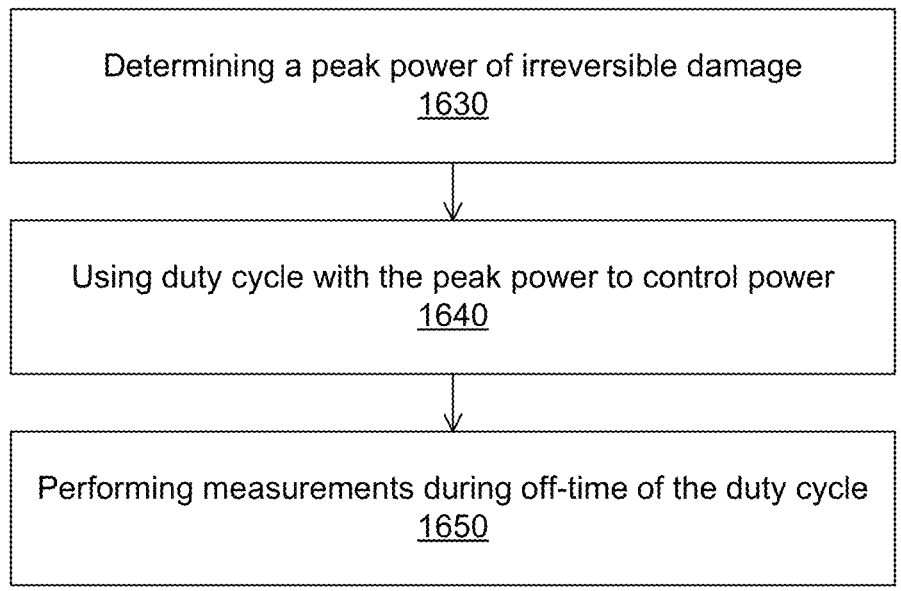

FIGS. 16A-16B illustrate flow charts for optimizing a surgery laser system according to some embodiments. In FIG. 16A, operation 1600 varies a power of a surgical laser by varying a duty cycle with a peak power. Operation 1610 performs measurements during off-time of the duty cycle.

In FIG. 16B, operation 1630 determines a peak power of irreversible damage. Operation 1640 uses duty cycle with the peak power to control power. Operation 1650 performs measurements during off-time of the duty cycle.

In some embodiments, the surgical laser system can be configured to have strong reaction with water. In living systems, in addition to the water molecules association with the electromagnetic field and effects of that, one has to consider the "meso-structure" effect where proteins and charged groups (located at specific sites on the proteins) are crucial for the overall biological activity. These specifically located charged groups associate with the water molecules and by doing this influence the dielectric behavior of the whole molecular-assembly, which in turn effects its biologic functioning. Thus, the dielectric properties of tissues (even at cellular level) depend on and vary with the water content.

In some embodiments, the surgical laser system can be configured for water and lipid absorption, such as using 1470 nm pulse lasers. The 1470 nm laser can have molecular and cellular interactions that are suitable for lipid and water absorption.

Figure 17A:
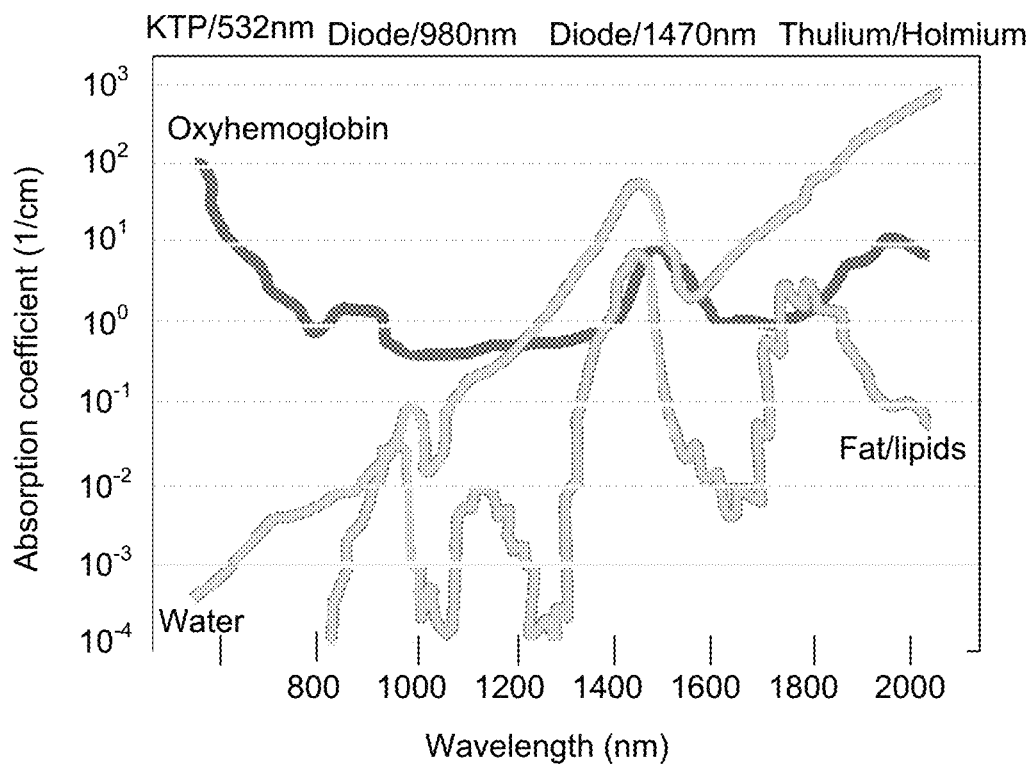
FIGS. 17A-17B illustrate effects of lasers with different wavelengths according to some embodiments.
Figure 17B:
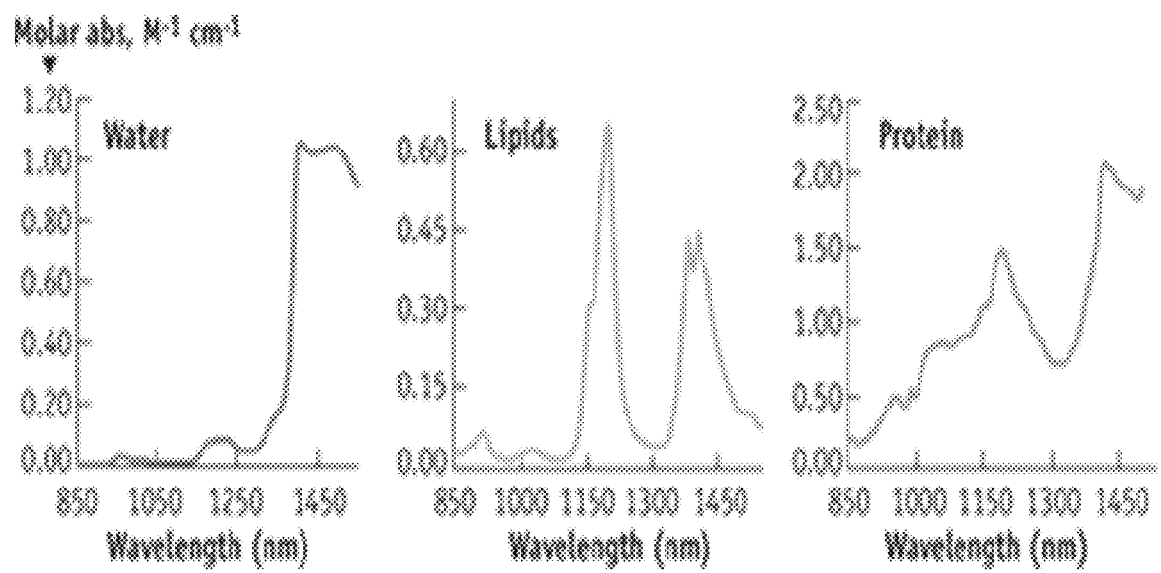

FIGS. 17A-17B illustrate effects of lasers with different wavelengths according to some embodiments. FIG. 17A shows an absorption chart of different materials. FIG. 17B shows absorption charts of water, lipid, and protein.

Lasers at 1470 nm in pulse mode can breakdown lipid structure. For example, it liquefies lipids and breakdown tissue permanently. In some embodiments, the present laser system is configured to control the heat transfer to avoid heat spreading deeper into the tissue. For example, the pulse width of the laser can be kept at less than 1 millisecond.

Lipids are insoluble in water and make up about half the weight of plasma membranes (Randall, 1997). Phospholipids and glycolipids are the prevalent lipids in the cell membrane.

Phospholipid is an amphipathic (containing a hydrophobic (water hating) and a hydrophilic (water loving) region) molecule. Phospholipids have a hydrophilic head, which is a phosphate group, and a hydrophobic tail containing a molecule of glycerol and two fatty acid chains. Glycolipids are lipids located on the surface of the cell membrane with a carbohydrate chain covalently bonded to them. Glycolipids play an important role in cell recognition. They act as markers or tags that help cells to differentiate between other cells in the body. They are able to recognize foreign cells. This feature is the basis for rejection of foreign cells as it appears in the immune system.

Proteins in the cell membrane are divided into integral proteins and peripheral proteins. Proteins that are embedded in the lipid bilayer are called integral proteins. Peripheral proteins are those that are loosely bound to the surface of the cell membrane. Next to phospholipids, proteins account for most of the mass of cell membranes.

Proteins found in the cell membrane perform different functions. A single protein molecule may carry out multiple functions. According to the tasks they carry out, membrane proteins are categorized into different classes (e.g. structural proteins, transport proteins, receptor proteins).

Proteins can determine most of the specific functions of the cell membrane. Some of these functions include transport of substances into the cell, communication of the cell with its outside environment, and cell recognition.

Figure 18A:
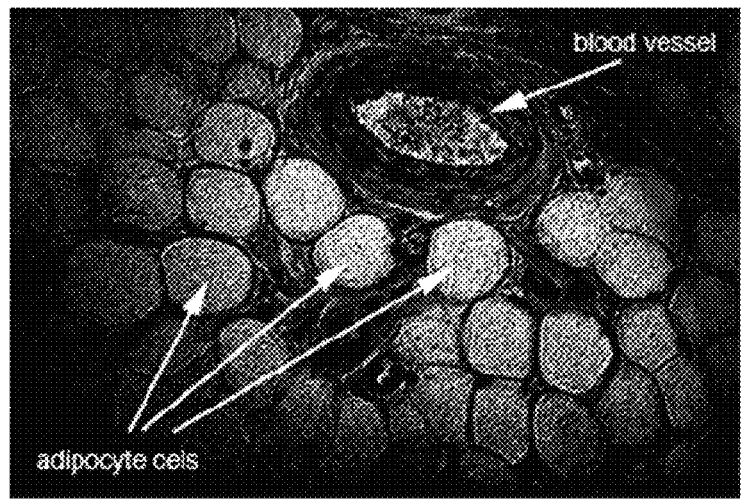
FIGS. 18A-18B illustrate configurations of tissue subjected to a surgical laser process.
Figure 18B:
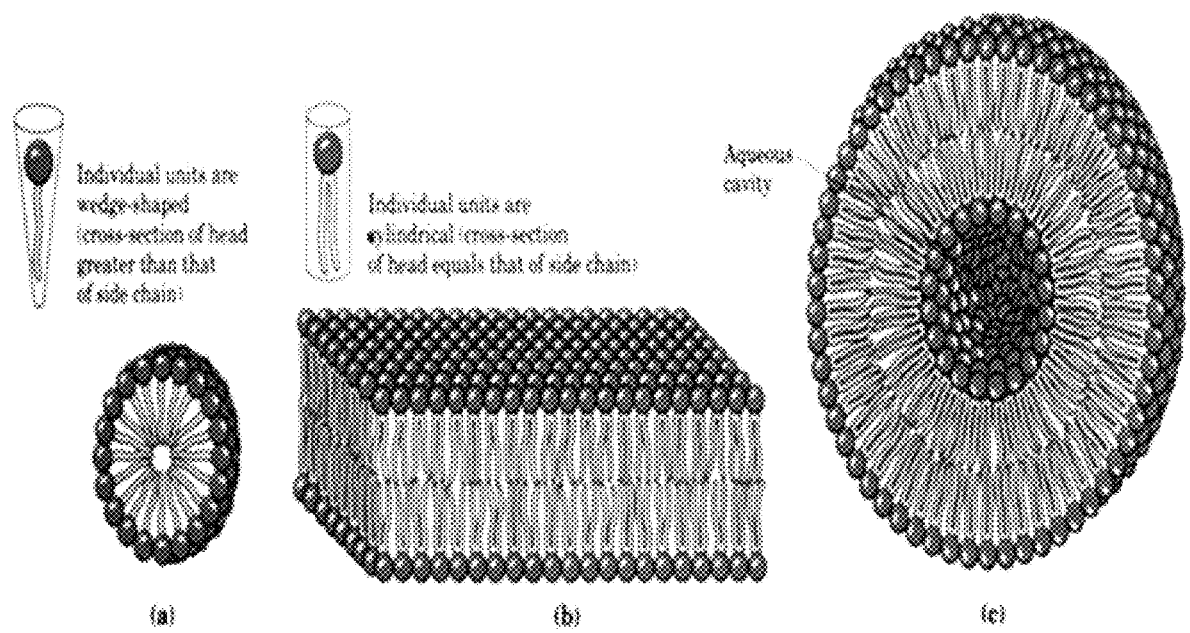

FIGS. 18A-18B illustrate configurations of tissue subjected to a surgical laser process. FIG. 18A shows relative positions of a blood vessel and the surrounding adipocyte cells. FIG. 18B shows amphipathic lipid aggregates that form in water. In spherical micelles (a), the hydrophobic chains of the fatty acids are sequestered at the core of the sphere. There is virtually no water in the hydrophobic interior of the micelle. In a bilayer (b), all acyl side chains except those at the edges of the sheet are protected from interaction with water. When an extensive two-dimensional bilayer folds on itself, it forms a liposome, a three-dimensional hollow vesicle enclosing an aqueous cavity (c).

What is claimed is:

1. A surgical laser system, comprising
a surgical laser assembly, wherein the surgical laser assembly comprises a first laser;
an optical assembly, wherein the optical assembly is configured to deliver an output of the first laser to a tissue;
an aiming laser assembly, wherein the aiming laser assembly comprises one or more second lasers configured to mark the tissue, wherein the aiming laser assembly is also configured to provide an excitation energy for a fluorescent process from the tissue or from a marker at the tissue location; wherein the aiming laser assembly comprises an aiming laser controller, wherein the aiming laser controller is configured to control the excitation energy provided by at least a laser of the one or more second lasers for the fluorescent process,
a fluorescent sensing assembly, wherein the fluorescent sensing assembly is configured to detect a fluorescent signal emitted from the tissue or from the marker;
a controller, wherein the controller is configured to process the fluorescent signal for assistance in controlling the surgical laser assembly.

2. A system as in claim 1 wherein the first laser is configured to deliver laser pulses at 1470 nm to 2140 nm wavelength.

3. A system as in claim 1 wherein the first laser is configured to perform a surgical operation on the tissue.

4. A system as in claim 1 wherein the aiming laser assembly comprises three second lasers having different colors.

5. A system as in claim 1 wherein the aiming laser assembly comprises an aiming laser controller, wherein the aiming laser controller is configured to control the one or more second lasers for selectively delivering one or a combination of the one or more second lasers.

6. A system as in claim 1 wherein the fluorescent sensing assembly comprises a hyperspectral or multispectral fluorescent sensor.

7. A system as in claim 1 wherein the controller is configured to provide processed information from the fluorescent signal to a display.

8. A system as in claim 1 wherein the controller is configured to use processed information from the fluorescent signal to control at least one of a power, a pulse rate, and a pulse width of the surgical laser assembly for operating on the tissue.

9. A system as in claim 1 further comprising at least one of a near infrared imaging assembly and a Raman spectrometer for characterizing the tissue.

10. A system as in claim 1 further comprising an infrared sensing assembly, wherein the infrared sensing assembly is configured to measure a rate of change of temperature with respect to time of the tissue.

11. A system as in claim 1 further comprising an infrared sensing assembly, wherein the controller is configured to control the surgical laser assembly to prevent overheating of the tissue based on a time rate of change of a signal from the infrared sensing assembly.

12. A system as in claim 1 further comprising an infrared sensing assembly, wherein the controller is configured to predict a temperature of the tissue based on a signal from the infrared sensing assembly, wherein the controller is configured to control at least a power, a pulse rate, and a pulse width of the first laser to prevent damage to the tissue due to overheating.

13. A system as in claim 1 further comprising an infrared sensing assembly, wherein the controller is configured to calculate a rate of change of a temperature of the tissue based on a signal from the infrared sensing assembly, wherein the controller is configured to control at least a power, a pulse rate, and a pulse width of the first laser to prevent the temperature of the tissue from overheating.

14. A system as in claim 1 wherein the controller is configured to perform measurements during off-time of laser pulses of the first laser.

15. A system as in claim 1 wherein the controller is configured to increase off-time of laser pulses of the first laser by maintaining a same power peak while reducing the laser pulse widths when decreasing a power of the first laser.

16. A system as in claim 1 wherein the controller is configured to maximize off-time of laser pulses of the first laser by maintaining a constant power of the first laser while changing the laser pulse widths when changing a power of the first laser.

17. A system as in claim 1 wherein the controller is configured to change a power of the first laser by discretely changing between multiple levels of power values, wherein the controller is configured to change a power of the first laser between two levels of power values of the multiple levels of power values by selecting a higher level of power value between the two levels of power values and by continuously changing a duty cycle.

* * * * *